(12) United States Patent
Reinke et al.

(10) Patent No.: US 10,610,694 B2
(45) Date of Patent: Apr. 7, 2020

(54) IMPLANTED ELECTRODE CONFIGURATION FOR PHYSIOLOGICAL SENSING AND TISSUE CONDUCTANCE COMMUNICATION

(71) Applicant: Medtronic, Inc., Minneapolis, MN (US)

(72) Inventors: James D. Reinke, Maple Grove, MN (US); James K. Carney, Roseville, MN (US); Can Cinbis, Salt Lake City, UT (US); Richard J. O'Brien, Hugo, MN (US); Bushan Purushothaman, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 415 days.

(21) Appl. No.: 15/411,360

(22) Filed: Jan. 20, 2017

(65) Prior Publication Data
US 2018/0207429 A1 Jul. 26, 2018

(51) Int. Cl.
| | |
|---|---|
| *A61N 1/375* | (2006.01) |
| *A61B 5/042* | (2006.01) |
| *H04B 13/00* | (2006.01) |
| *A61B 5/00* | (2006.01) |
| *A61N 1/372* | (2006.01) |
| *A61N 1/39* | (2006.01) |
| *A61N 1/37* | (2006.01) |
| *A61B 5/0402* | (2006.01) |

(52) U.S. Cl.
CPC .......... *A61N 1/3756* (2013.01); *A61B 5/0028* (2013.01); *A61B 5/0422* (2013.01); *A61B 5/6867* (2013.01); *A61N 1/37211* (2013.01); *A61N 1/3962* (2013.01); *H04B 13/005* (2013.01); *A61B 5/0402* (2013.01); *A61B 2562/0209* (2013.01); *A61N 1/3702* (2013.01); *A61N 1/37205* (2013.01)

(58) Field of Classification Search
CPC ........................... A61N 1/3756; A61N 1/0028
USPC ........................................................ 607/60
See application file for complete search history.

(56) References Cited

U.S. PATENT DOCUMENTS

| | | | |
|---|---|---|---|
| 4,844,099 | A | 7/1989 | Skalsky et al. |
| 4,987,897 | A | 1/1991 | Funke |
| 5,113,859 | A | 5/1992 | Funke |
| 5,849,031 | A | 12/1998 | Martinez et al. |
| 5,987,352 | A | 11/1999 | Klein et al. |

(Continued)

FOREIGN PATENT DOCUMENTS

WO 2016118847 A1 7/2016

OTHER PUBLICATIONS (PCT/US2018/014190) PCT Notification of Transmittal of the International Search Report and the Written Opinion of the International Searching Authority, dated Jun. 7, 2018, 12 pages.

*Primary Examiner* — Nadia A Mahmood

(57) ABSTRACT

In some examples, the disclosure describes an implantable medical device comprising a plurality of electrodes, sensing circuitry configured to sense a physiological electrical signal via the plurality of electrodes, and communication circuitry configured to transmit and/or receive a transconductance communication signal via the plurality of electrodes, wherein at least one electrode of the plurality of electrodes comprises a lower-capacitance portion and a higher-capacitance portion.

28 Claims, 17 Drawing Sheets

(56) References Cited

U.S. PATENT DOCUMENTS

| | | | |
|---|---|---|---|
| 5,996,111 | A | 11/1999 | Yoshida et al. |
| 6,871,091 | B2 | 3/2005 | Wilkinson et al. |
| 6,901,297 | B2 | 5/2005 | Frericks et al. |
| 6,944,489 | B2 | 9/2005 | Zeijlemaker et al. |
| 6,999,821 | B2 | 2/2006 | Jenney et al. |
| 7,720,550 | B2 | 5/2010 | Sommer et al. |
| 7,801,623 | B2 | 9/2010 | McVenes et al. |
| 7,899,552 | B2 | 3/2011 | Atanasoska et al. |
| 8,017,179 | B2 | 9/2011 | Atanasoska et al. |
| 8,117,179 | B2 | 2/2012 | Simpson et al. |
| 8,150,517 | B2 | 4/2012 | Dal Molin et al. |
| 8,412,352 | B2 | 4/2013 | Griswold et al. |
| 8,515,559 | B2 | 8/2013 | Roberts et al. |
| 8,916,004 | B2 | 12/2014 | Hintz et al. |
| 8,996,111 | B2 | 3/2015 | Marshall et al. |
| 9,079,037 | B2 | 7/2015 | Martinez et al. |
| 2006/0020316 | A1 | 1/2006 | Martinez et al. |
| 2008/0009905 | A1 | 1/2008 | Zeijlemaker |
| 2010/0292744 | A1 | 11/2010 | Hill et al. |
| 2010/0305675 | A1 | 12/2010 | Laske et al. |
| 2012/0109258 | A1 | 5/2012 | Cinbis et al. |
| 2012/0197350 | A1 | 8/2012 | Roberts et al. |
| 2015/0196769 | A1 | 7/2015 | Stahmann et al. |
| 2015/0251000 | A1 | 9/2015 | Kane et al. |
| 2015/0306375 | A1 | 10/2015 | Marshall et al. |
| 2015/0314130 | A1 | 11/2015 | Martinez et al. |
| 2016/0121106 | A1 | 5/2016 | Marshall et al. |
| 2016/0144190 | A1* | 5/2016 | Cao .................... A61N 1/36514 607/17 |
| 2016/0250483 | A1 | 9/2016 | Klimovitch et al. |

* cited by examiner

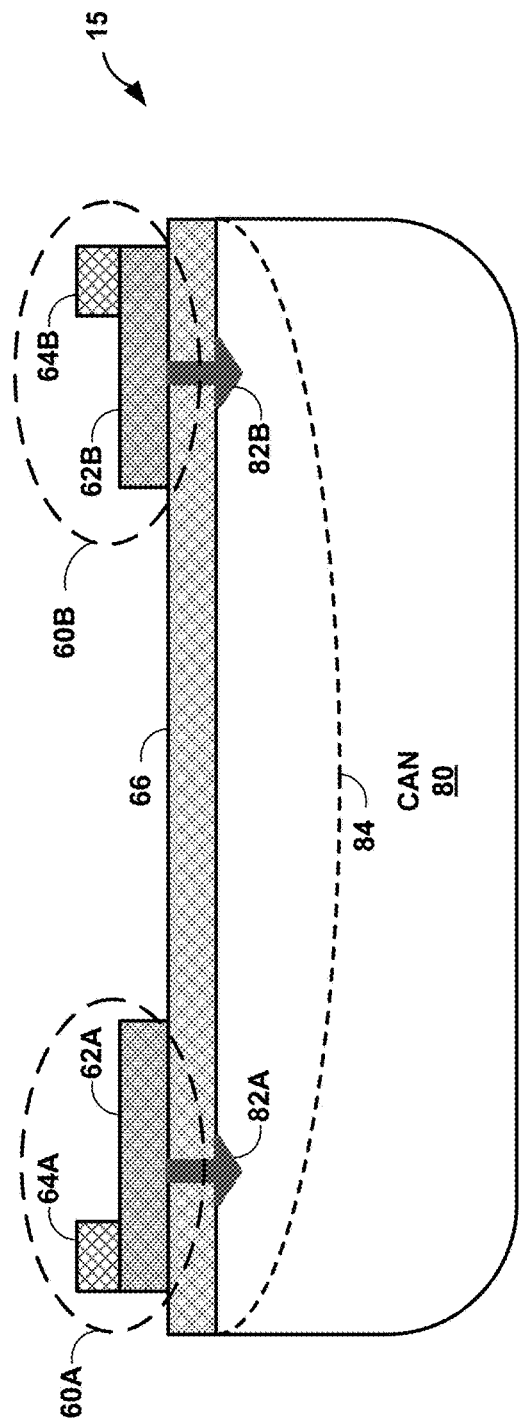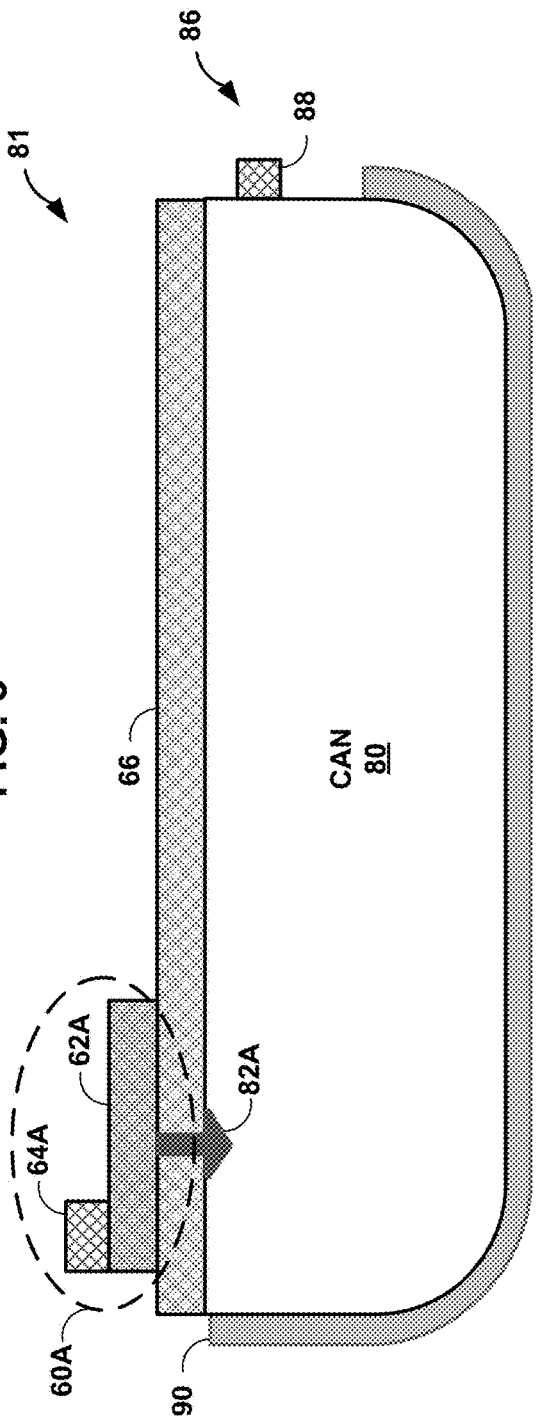

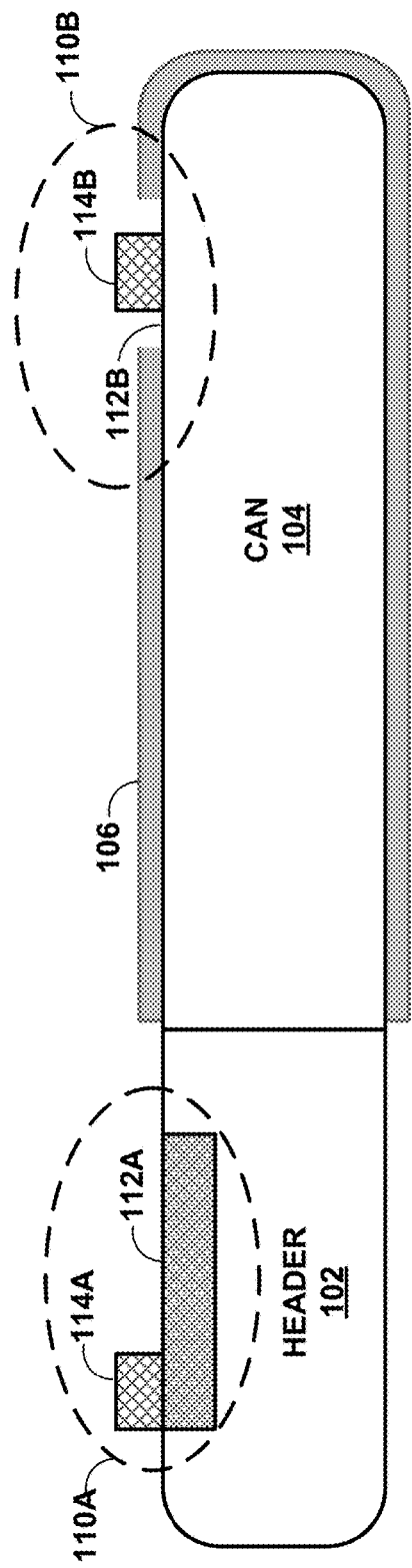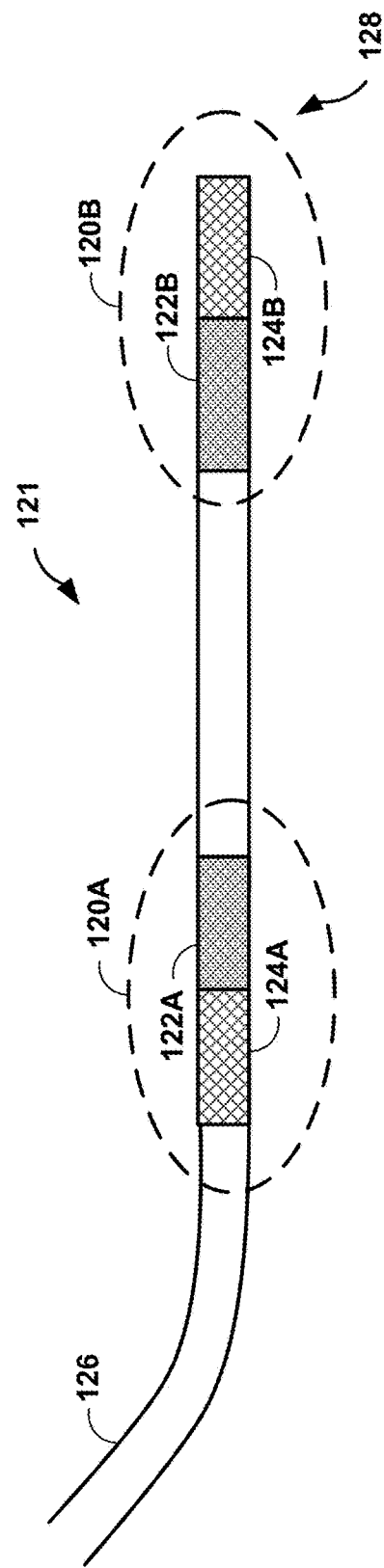

US 10,610,694 B2

IMPLANTED ELECTRODE CONFIGURATION FOR PHYSIOLOGICAL SENSING AND TISSUE CONDUCTANCE COMMUNICATION

TECHNICAL FIELD

The disclosure relates to implantable medical devices and, in particular electrode configurations for wireless communication and wireless sensing by implantable medical devices.

BACKGROUND

A wide variety of implantable medical devices (IMDs) that deliver a therapy to or monitor a physiologic or biological condition of a patient, or both, have been clinically implanted or proposed for clinical implantation in patients. An IMD may deliver therapy to and/or monitor a physiological or biological condition with respect to a variety of organs, nerves, muscles or tissues of the patients, such as the heart, brain, stomach, spinal cord, pelvic floor, or the like. The therapy provided by the IMD may include electrical stimulation therapy, drug delivery therapy, or therapy to reduce or eliminate a condition or symptoms of the condition of the patient.

The IMD may wirelessly communicate with another implanted device or an external device. An external device with which an IMD may communicate may be a programming device or a monitoring device (e.g., either attached to the patient or otherwise located near the patient). The information exchanged may be information related to a condition of the patient, such as physiological signals measured by one or more sensors, or information related to a therapy delivered to the patient. This information may be previously stored or real-time information. The IMD may also receive information from the external device, such as configuration information that may be used to configure a therapy to be provided to the patient. An IMD may communicate with another implanted device to control the operation of the other implanted device and/or to receive physiological data sensed by the other implanted device.

In some examples, an IMD wirelessly communicates with an implanted or external device via tissue conductance communication (TCC). During TCC, current is driven through the tissue between two or more electrodes of the transmitting IMD (or external device). The current spreads through the thorax, producing a potential field. The receiving IMD (or external device) may detect the TCC signal by measuring the potential difference between two or more of its electrodes.

SUMMARY

In general, this disclosure is directed to techniques for improving the sensing of physiological electrical signals and the transmission and receipt of TCC signals via electrodes of an implantable medical device. For lower frequency physiological electrical signals, the electrodes, or active portion of the electrodes, may be spaced apart for a longer dipole and higher amplitudes. For higher frequency TCC signals, the surface area of the electrodes, or active portion of the electrodes, may be expanded to reduce the impedance of the electrodes, thereby increasing the current capability. Additionally, in some examples, the surface area of the electrodes, or active portion of the electrodes, may be smaller for delivery of lower frequency electrical stimulation therapy.

As one example, the disclosure is directed to an implantable medical device comprising a plurality of electrodes, sensing circuitry configured to sense a physiological electrical signal via the plurality of electrodes, and communication circuitry configured to transmit and/or receive a tissue conductance communication (TCC) signal via the plurality of electrodes, wherein at least one electrode of the plurality of electrodes comprises a lower-capacitance portion and a higher-capacitance portion.

In some examples, the disclosure is directed to a method for manufacturing an implantable medical device, the method comprising forming a first material of an electrode of the implantable medical device, depositing a mask on at least part of the first material, depositing a second material on the mask and the first material to form a higher-capacitance portion of the electrode, and removing the mask from the first material to expose a lower-capacitance portion of the electrode.

In some examples, the disclosure is directed to a method for manufacturing an implantable medical device, the method comprising: forming an electrode on the implantable medical device; depositing a mask on a first portion of the electrode; depositing a dielectric material on the mask and a second portion of the electrode; and removing the mask from the first portion of the electrode and leaving the dielectric material on the second portion of the electrode, wherein the first portion of the electrode has a higher capacitance than the second portion of the electrode.

In some examples, an implantable medical device comprises at least four electrodes, sensing circuitry configured to sense a physiological electrical signal via a first electrode and a second electrode of the at least four electrodes, communication circuitry configured to transmit a transconductance communication signal via at least a third electrode and a fourth electrode of the at least four electrodes; and switching circuitry configured to connect the first electrode and the second electrode to the sensing circuitry, and connect the at least four electrodes to the communication circuitry. The implantable medical device also comprises processing circuitry configured to control the switching circuitry to connect the first electrode and the second electrode to the sensing circuitry to sense the physiological electrical signal, and control the switching circuitry to connect at least the third electrode and the fourth electrode to the communication circuitry to transmit or receive tissue conductance communication (TCC) signals.

As another example, the disclosure is directed to method for operating an implantable medical device, the method comprising: controlling switching circuitry of the implantable medical device to connect a first electrode and a second electrode to sensing circuitry of the implantable medical device; sensing a physiological electrical signal via the first electrode and the second electrode; controlling the switching circuitry to connect at least a third electrode and a fourth electrode to communication circuitry of the implantable medical device; transmitting tissue conductance communication (TCC) signals via at least the third electrode and the fourth electrode; and receiving TCC signals via at least the third electrode and the fourth electrode.

This summary is intended to provide an overview of the subject matter described in this disclosure. It is not intended to provide an exclusive or exhaustive explanation of the apparatus and methods described in detail within the accompanying drawings and description below. The details of one or more aspects of the disclosure are set forth in the accompanying drawings and the description below.

BRIEF DESCRIPTION OF DRAWINGS

The details of one or more examples of this disclosure are set forth in the accompanying drawings and the description below. Other features, objects, and advantages of this disclosure will be apparent from the description and drawings, and from the claims.

FIG. 3 is a side-view conceptual diagram of an example configuration of an implantable medical device including two electrodes.

FIG. 4 is a side-view conceptual diagram of another example configuration of an implantable medical device including two electrodes.

FIG. 5 is a side-view conceptual diagram of another example configuration of an implantable medical device including two electrodes.

FIG. 6 is a conceptual diagram illustrating an example configuration of an implantable medical lead including an electrode and a tip electrode.

Figure 1A:
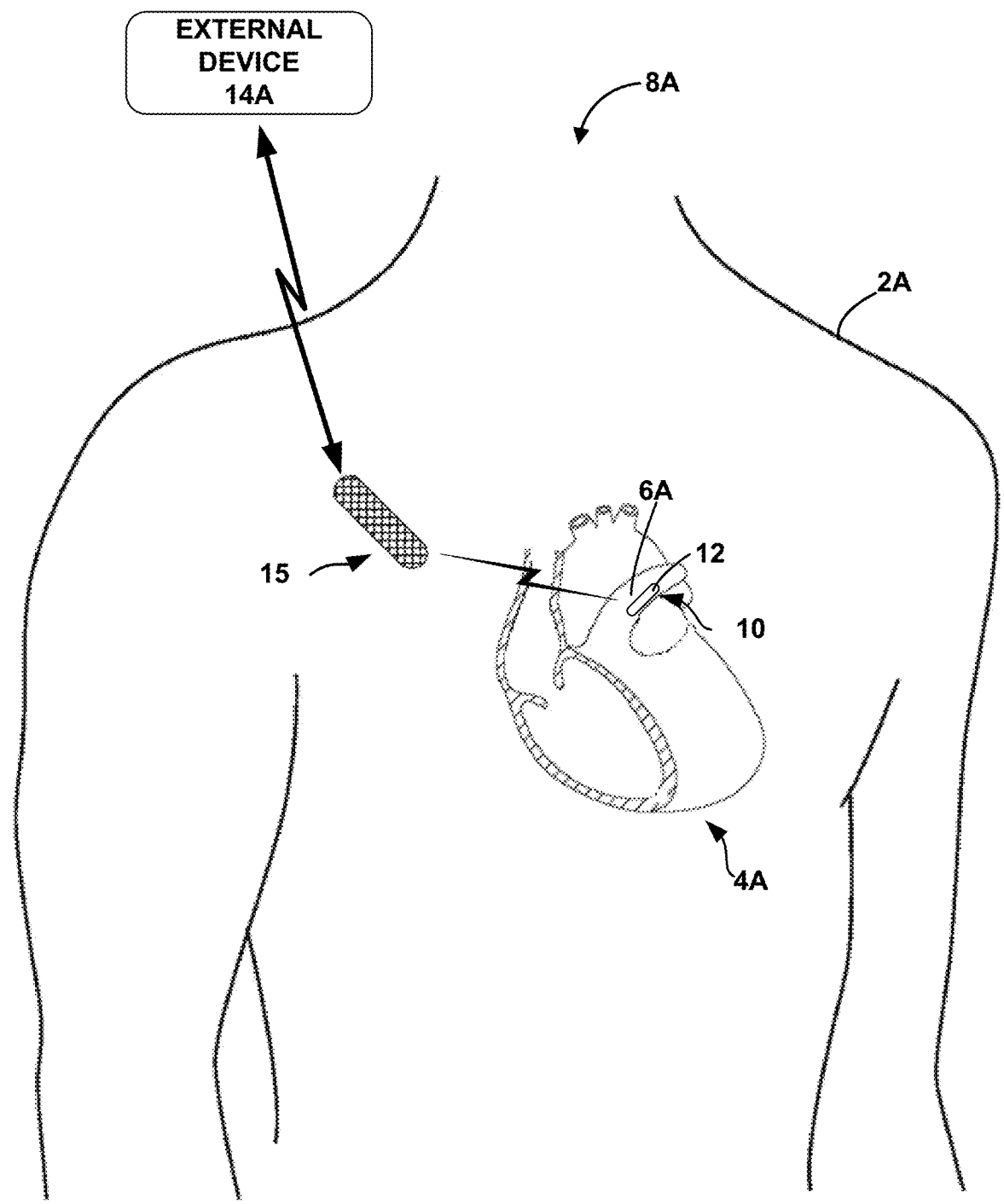
FIG. 1A is a conceptual drawing illustrating an example medical device system in conjunction with a patient.

The drawings and the description provided herein illustrate and describe various examples of the inventive methods, devices, and systems of the present disclosure. However, the methods, devices, and systems of the present disclosure are not limited to the specific examples as illustrated and described herein, and other examples and variations of the methods, devices, and systems of the present disclosure, as would be understood by one of ordinary skill in the art, are contemplated as being within the scope of the present application.

DETAILED DESCRIPTION

An implantable medical device (IMD) may transmit and receive signals at high and low frequencies for communication, sensing physiological signals, and delivering therapeutic signals. For example, the IMD may sense heart beat signals and transmit and/or receive tissue conductance communication (TCC) signals. For low-frequency signals, such as sensing physiological signals, the IMD may include relatively smaller surface area electrodes spaced at a relatively long dipole length, resulting in higher amplitude of the low-frequency signals. For relatively high-frequency signals, such as transmitting TCC signals, the IMD may include larger electrodes for a reduced load and source impedance to enable higher current capability during TCC signal transmission and higher received signal strength during TCC signal reception as well as reduced power consumption.

The IMD may include an electrode for receiving physiological electrical signals and transmitting and receiving TCC signals. The electrode may include a higher-capacitance portion configured to transmit and receive both relatively lower-frequency and relatively higher-frequency signals. The higher-capacitance portion of the electrode may provide a relatively lower impedance at both relatively lower frequencies and relatively higher frequencies. The electrode may also include a relatively lower-capacitance portion configured to transmit and receive relatively higher-frequency signals. The lower-capacitance portion of the electrode may provide a relatively higher impedance at relatively lower frequencies and a relatively lower impedance at relatively higher frequencies, such that the lower-capacitance portion of the electrode may not significantly affect, e.g., participate in or be active during, the receipt of lower-frequency signals, e.g., physiological electrical signals, by the higher-capacitance portion of the electrode. For purposes of this disclosure, low impedance or lower impedance may be defined as less than one thousand ohms.

The techniques of this disclosure may allow for a relatively long dipole length between the higher-capacitance portions of one or more electrodes, while increasing the effective surface area of the one or more electrodes for higher-frequency signals. The longer dipole length at relatively lower frequencies creates a higher transimpedance and higher amplitude for low-frequency signals. The relatively larger surface area of the electrode at high frequencies effectively lowers the impedance seen by higher-frequency signals, enabling higher current capability during TCC transmission and higher received signal strength during TCC reception. Lower impedance may also reduce the power consumption of the IMD when communicating via higher frequencies. For purposes of this disclosure, lower-frequency signals may include frequencies less than about one hundred Hertz (Hz), and higher-frequency signals may include frequencies greater than about fifty kiloHertz (kHz).

FIG. 1A is a conceptual drawing illustrating an example medical device system 8A in conjunction with a patient 2A. In the illustrated example, medical device system 8A includes an implantable medical device (IMD) 15, also referred to as implantable monitoring device 15 or an implantable hub device, in communication with external device 14A. Medical device system 8A also includes implantable pressure sensing device 12, also referred to as sensor device 12. For purposes of this description, knowledge of cardiovascular anatomy is presumed and details are omitted except to the extent necessary or desirable to explain the context of the techniques of this disclosure.

As shown in FIG. 1A, implantable sensor assembly 10, including sensor device 12, may be implanted within pulmonary artery 6A of heart 4A. In some examples, sensor assembly 10 is implanted within a left pulmonary artery, whereas in other examples, sensor assembly 10 is implanted within a right pulmonary artery. For the sake of clarity, a fixation assembly for sensor assembly 10 is not depicted in FIG. 1A.

In the illustrated example, IMD 15 is an insertable cardiac monitor (ICM) capable of sensing and recording cardiac electrogram (EGM) signals from a position outside of heart 4A via electrodes, and will be referred to as ICM 15 hereafter. In some examples, ICM 15 includes or is coupled to one or more additional sensors, such as accelerometers, that generate one or more signals that vary based on patient motion and/or posture, blood flow, or respiration. ICM 15 may monitor a physiological parameter indicative of patient state, such as posture, heart rate, activity level, heart rate, and/or respiration rate. ICM 15 may be implanted outside of the thorax of patient 2A, e.g., subcutaneously or submuscularly, such as the pectoral location illustrated in FIG. 1A. In some examples, ICM 15 may take the form of a Reveal LINQ™ ICM, available from Medtronic plc, of Dublin, Ireland.

Sensor device 12 may be implanted, as one example, within a pulmonary artery of patient 2A and may include pressure sensing circuitry configured to measure the cardiovascular pressure of patient 2A. In some examples, sensor device 12 may be a part of sensor assembly 10. If sensor device 12 determines that the current time is within a predetermined window that may be stored in memory of sensor device 12, sensor device 12 may measure and transmit the cardiovascular pressure of patient 2A to ICM 15. In some examples, sensor device 12 may autonomously store the pressure measurement data and transmit the stored data to ICM 15 at some time after the time of measurement. In some examples, sensor device 12 may include wireless communication circuitry configured to receive a trigger signal from ICM 15 via TCC. The pressure sensing circuitry of sensor device 12 may be configured to measure the cardiovascular pressure of patient 2A in response to receiving the trigger signal. In either case, sensor device 12 may be configured to transmit the measured pressure values to ICM 15 via TCC.

ICM 15 may transmit measurements and data acquired by ICM 15 or sensor device 12 to external device 14A. ICM 15 may also receive signals from external device 14A. In some examples, ICM 15 may communicate with external device 14A and sensor device 12 via RF signals and/or TCC.

External device 14A may be a computing device, e.g., used in a home, ambulatory, clinic, or hospital setting, to wirelessly communicate with ICM 15. External device 14A may be coupled to a remote patient monitoring system, such as Carelink®, available from Medtronic plc, of Dublin, Ireland. External device 14A may be, as examples, a programmer, external monitor, or consumer device, e.g., smart phone.

External device 14A may be used to program commands or operating parameters into ICM 15 for controlling its functioning, e.g., when configured as a programmer for ICM 15. External device 14A may be used to interrogate ICM 15 to retrieve data, including device operational data as well as physiological data accumulated in IMD memory. The interrogation may be automatic, e.g., according to a schedule, or in response to a remote or local user command. Examples of communication techniques used by ICM 15 and external device 14A include TCC or RF telemetry, which may be an RF link established via Bluetooth, WiFi, or medical implant communication service (MICS).

Figure 1B:
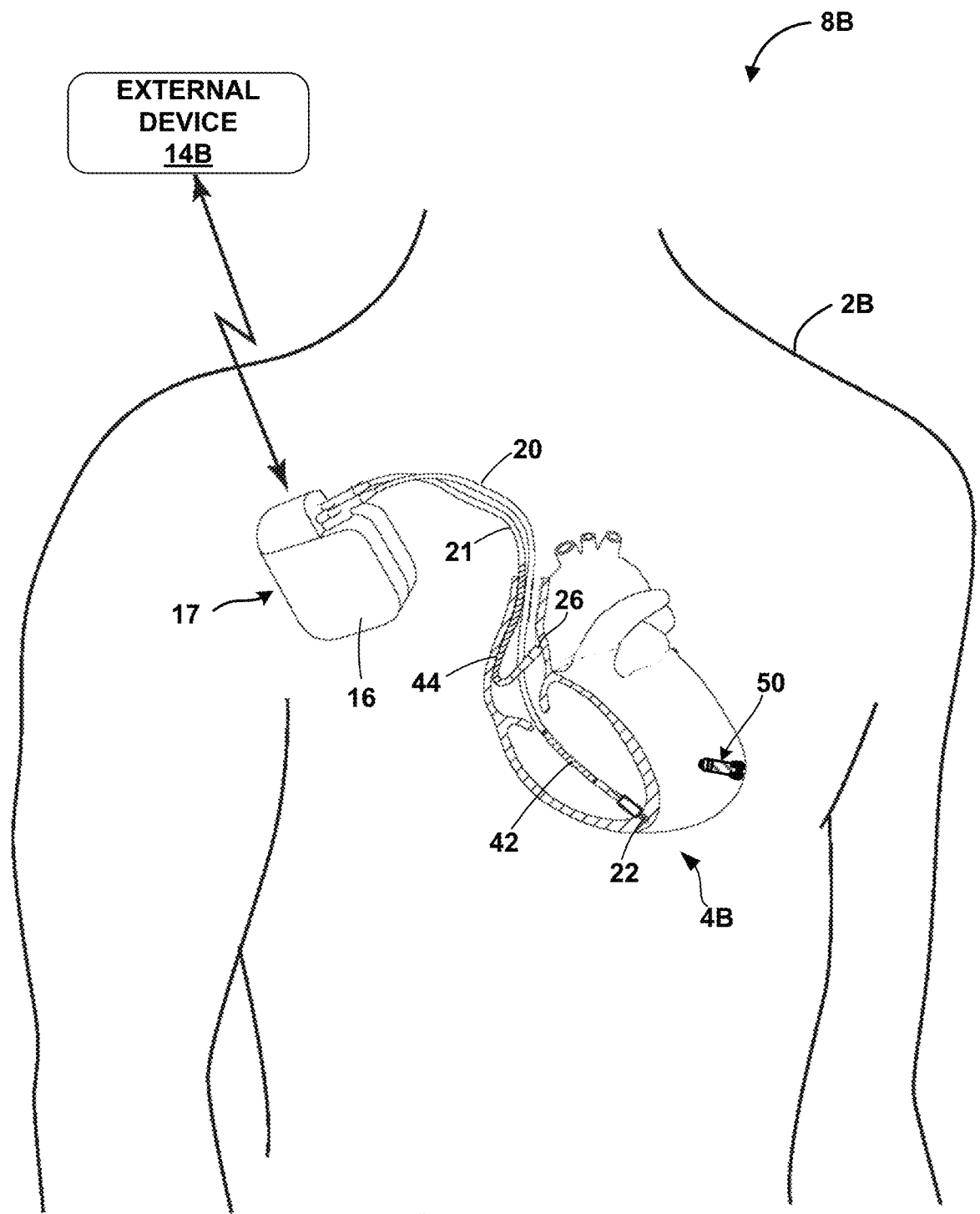
FIG. 1B is a conceptual drawing illustrating another example medical device system in conjunction with a patient.

FIG. 1B is a conceptual drawing illustrating another example medical device system 8B in conjunction with a patient 2B. In the illustrated example, medical device system 8B includes an IMD 17 coupled to a ventricular lead 20 and an atrial lead 21. IMD 17 is an implantable cardioverter-defibrillator (ICD) capable of delivering pacing, cardioversion and defibrillation therapy to the heart 4B of a patient 2B, and will be referred to as ICD 17 hereafter.

Ventricular lead 20 and atrial lead 21 are electrically coupled to ICD 17 and extend into the patient's heart 4B. Ventricular lead 20 includes electrodes 22 and 42 shown positioned on the lead in the patient's right ventricle (RV) for sensing ventricular EGM signals and pacing in the RV. Atrial lead 21 includes electrodes 26 and 44 positioned on the lead in the patient's right atrium (RA) for sensing atrial EGM signals and pacing in the RA. Electrodes 42 and 44 may also be configured as coil electrodes and used to deliver cardioversion and defibrillation shocks. The term "anti-tachyarrhythmia shock" may be used herein to refer to both cardioversion shocks and defibrillation shocks.

ICD 17 may use both ventricular lead 20 and atrial lead 21 to acquire cardiac electrogram (EGM) signals from patient 2B and to deliver therapy in response to the acquired data. Medical device system 8B is shown as having a dual chamber ICD configuration, but other examples may include one or more additional leads, such as a coronary sinus lead extending into the right atrium, through the coronary sinus and into a cardiac vein to position electrodes along the left ventricle (LV) for sensing LV EGM signals and delivering pacing pulses to the LV. In other examples, a medical device system may be a single chamber system, or otherwise not include atrial lead 21.

Processing circuitry, sensing circuitry, and other circuitry configured for performing the techniques described herein are housed within a sealed housing 16. Housing 16 (or a portion thereof) may be conductive so as to serve as an electrode for pacing or sensing or as an active electrode during defibrillation. As such, housing 16 is also referred to herein as "housing electrode" 16. Housing 16 may include one or more electrodes with a higher-capacitance portion and a lower-capacitance portion. The higher-capacitance portion and the lower-capacitance portion may be formed using two different materials.

ICD 17 may transmit EGM signal data and cardiac rhythm episode data acquired by ICD 17, as well as data regarding delivery of therapy by ICD 17, to an external device 14B. External device 14B may be a computing device, e.g., used in a home, ambulatory, clinic, or hospital setting, to communicate with ICD 17 via wireless telemetry. External device 14B may be coupled to a remote patient monitoring system, such as Carelink®, available from Medtronic plc, of Dublin, Ireland. External device 14B may be, as examples, a programmer, external monitor, or consumer device, e.g., smart phone.

External device 14B may be used to program commands or operating parameters into ICD 17 for controlling its functioning, e.g., when configured as a programmer for ICD 17. External device 14B may be used to interrogate ICD 17 to retrieve data, including device operational data as well as physiological data accumulated in IMD memory. The interrogation may be automatic, e.g., according to a schedule, or in response to a remote or local user command. Examples of communication techniques used by ICD 17 and external device 14B include TCC and RF telemetry, which may be an RF link established via Bluetooth, WiFi, or medical implant communication service (MICS).

In some examples, as illustrated in FIG. 1B, medical device system 8B may also include an intracardiac pacing device (IPD) 50. In the illustrated example, IPD 50 is implanted in the left-ventricle of patient 2B. In some examples, one or more IPDs 50 may additionally or alternatively be implanted within other chambers of heart 4B, or attached to the heart epicardially, or in other anatomical areas of interest such as the pulmonary artery.

IPD 50 is configured to sense electrical activity of heart 4B and deliver pacing therapy, e.g., bradycardia pacing therapy, cardiac resynchronization therapy (CRT), anti-tachycardia pacing (ATP) therapy, and/or post-shock pacing, to heart 4B. IPD 50 may be attached to an interior wall of heart 4B via one or more fixation elements that penetrate the tissue. These fixation elements may secure IPD 50 to the cardiac tissue and retain an electrode (e.g., a cathode or an anode) on the housing of IPD 50 in contact with the cardiac tissue. In addition to delivering pacing pulses, IPD 50 may be capable sensing electrical signals using the electrodes carried on the housing of IPD 50. These electrical signals may be electrical signals generated by cardiac muscle and indicative of depolarizations and repolarizations of heart 4B at various times during the cardiac cycle.

In some examples, ICD 17 and IPD 50 may both be configured to deliver pacing therapy. In such examples, ICD 17 and IPD 50 may delivery pacing therapy to the right and left ventricles of heart 4B, respectively, to provide CRT pacing. Additionally, ICD 17 and IPD 50 may both be configured to detect tachyarrhythmias, and deliver anti-tachyarrhythmia therapy.

ICD 17 and IPD 50 may be configured to coordinate their cardiac rhythm detection and treatment activities. In some examples, ICD 17 and IPD 50 may engage in wireless communication to facilitate such coordinated activity. The wireless communication may be via TCC, and may be one-way communication in which one device is configured to transmit communication messages and the other device is configured to receive those messages, or two-way communication in which each device is configured to transmit and receive communication messages.

In some examples, medical device system 8B may include one or more devices depicted in FIG. 1B. Alternatively or additionally, medical device system 8B may include devices not depicted in FIG. 1B. For example, ICD 17 may be a subcutaneous ICD or a substernal ICD that has a subcutaneous lead or a lead with a distal end under the sternum.

In some examples, medical device system 8B may include a single device, such as a pressure sensing device, an ICM, an IPD, and/or any other suitable device. The single device may be configured to communication via TCC signals with an external device. In some examples, medical device system 8B may include two IPDs configured to coordinate the heart rate of patient 2B using dual chamber sensing and/or pacing.

Figure 2:
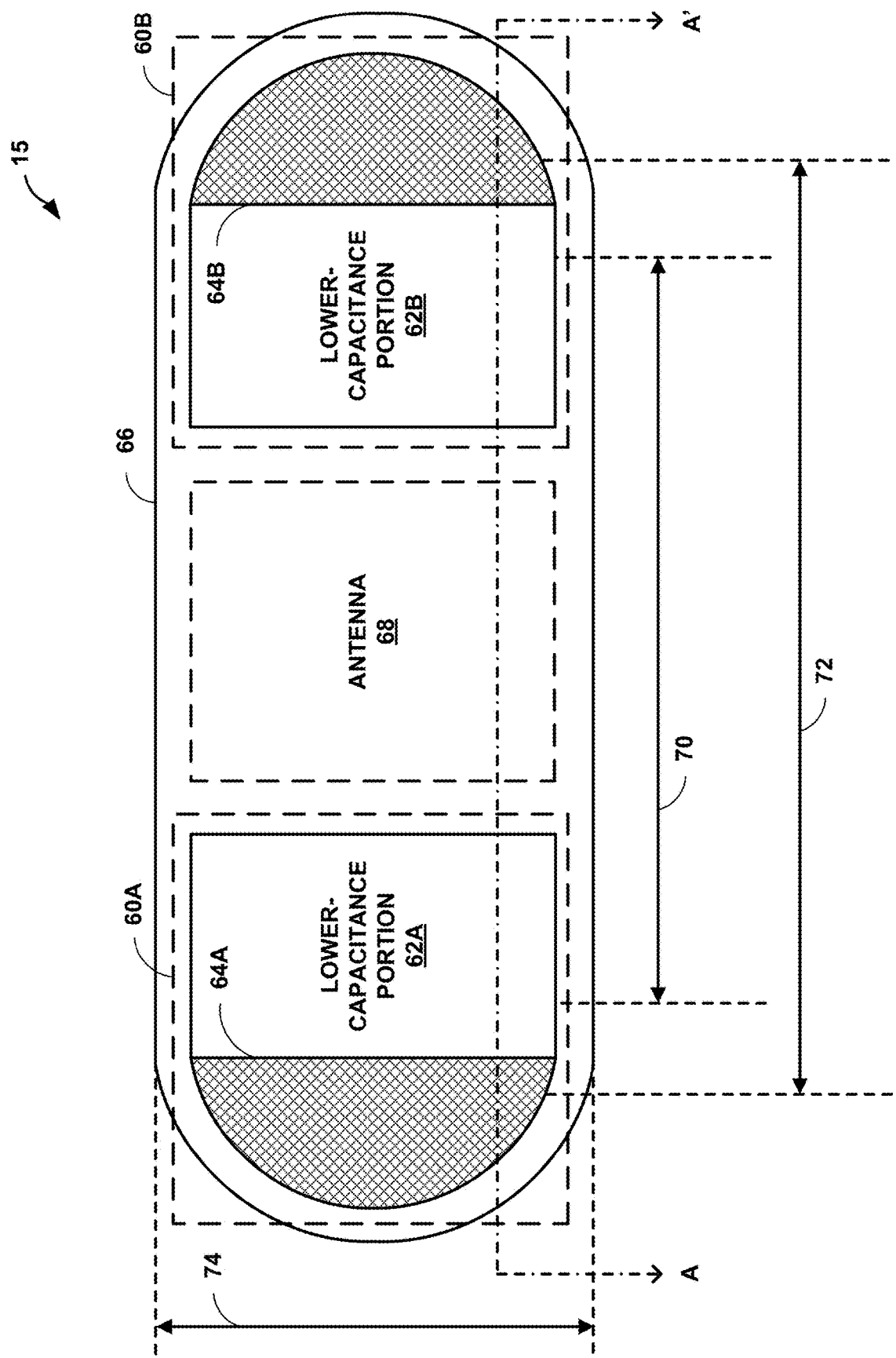
FIG. 2 is a top-view conceptual diagram of an example configuration of ICM of FIG. 1A.

FIG. 2 is a top-view conceptual diagram of an example configuration of ICM 15 of FIG. 1A. In the illustrated example, ICM 15 includes two electrodes 60A, 60B formed on an insulative cover 66 of the housing of ICM 15, and an antenna 68, which may be below insulative cover 66 and within the housing. In some examples, ICM 15 may not include insulative cover 66, such as if ICM 15 includes metallic housing. ICM 15 may include other components, including internal components and/or external components, that are not depicted in FIG. 2. Antenna 68 may be optional, and used for RF communication with external device 14A.

When IMD 15 is sensing relatively lower-frequency physiological electrical signals, such as an electrical signal of the heart including an R-wave, higher-capacitance portions 64A, 64B of electrodes 60A, 60B may receive the physiological electrical signals. Higher-capacitance portions 64A, 64B may present relatively lower impedance for relatively lower-frequency signals. Higher-capacitance portions 64A, 64B may be positioned at the distal ends of insulative cover 66 to increase the dipole length 72 for sensing physiological electrical signals, which may increase the amplitude of signals sensed by higher-capacitance portions 64A, 64B. Signal amplitude may be approximately proportional to the dipole length between the active portions of electrodes 60A, 60B, which in the case of lower-frequency signals is dipole length 72 between higher-capacitance portions 64A, 64B.

Higher-capacitance portions 64A, 64B may include a relatively higher-capacitance material such as titanium nitride. Titanium-nitride can be deposited in a manner to form three-dimensional structures, effectively increasing the surface area of an electrode. A capacitor (known as a double-layer capacitor) is formed when the titanium-nitride is placed in an ionic medium. In some examples, the increased surface area results in higher capacitance than for the bare metal. In some examples, each of higher-capacitance portions 64A, 64B may have a capacitance per unit area of greater than approximately one microfarad per square millimeter. In some examples, higher-capacitance portions 64A, 64B may include a cutoff frequency of less than fifty mHz to allow for sensing of relatively lower-frequency signals. Assuming a surface area of eleven square millimeters for higher-capacitance portions 64A, 64B, a fifty-mHz signal may be attenuated by 1.4 dB compared to a hypothetical electrode with infinite capacitance per unit area.

It may be desirable for higher-capacitance portions 64A, 64B to include a capacitance of less than three hundred nanofarads at five hundred mHz to allow an ECG amplifier to drive a one megaohm impedance at frequencies down to five hundred mHz. The ratio of capacitances between higher-capacitance portions 64A, 64B and lower-capacitance portions 62A, 62B may be larger than ten for a range of frequencies from five hundred mHz to one hundred Hz to ensure that higher-capacitance portions 64A, 64B include much lower impedance than lower-capacitance portions 62A, 62B at these frequencies. The capacitance of the lower-capacitance portions 62A, 62B may be higher than ten nanofarads at one hundred kHz so that the impedance of lower-capacitance portions 62A, 62B may be less than two hundred ohms at one hundred kHz.

When IMD 15 is transmitting or receiving relatively higher-frequency signals, such as TCC signals, higher-capacitance portions 64A, 64B and lower-capacitance portions 62A, 62B of electrodes 60A, 60B may transmit and receive the signals. Lower-capacitance portions 62A, 62B may include low impedance for relatively high-frequency signals, such as TCC signals, which may include a frequency between about fifty kHz and two hundred kHz, as examples. Thus, higher-capacitance portions 64A, 64B may be configured to sense physiological electrical signals and transmit or receive TCC signals, and lower-capacitance portions 62A, 62B may be configured to transmit or receive TCC signals but generally not sense physiological electrical signals. By using both higher-capacitance portions 64A, 64B and lower-capacitance portions 62A, 62B to transmit and receive high-frequency signals, the effective surface area for higher-frequency signals may be larger than the effective surface area for lower-frequency signals.

In some examples, each of lower-capacitance portions 62A, 62B may have a larger percentage of the surface area of electrodes 60A, 60B than each of higher-capacitance portions 64A, 64B. In some examples, the surface area of each of lower-capacitance portions 62A, 62B may be at least approximately 50%, 100%, or 200% larger than the surface area of one of higher-capacitance portions 64A, 64B. Lower-capacitance portions 62A, 62B may include material such as titanium (i.e., bare titanium). A capacitor (known as a double-layer capacitor) is formed when the bare titanium is placed in an ionic medium. Alternatively, the titanium can be oxidized to form titanium dioxide, which acts as the dielectric of the capacitor. Another method to form the lower-capacitance portions 62A, 62B is to deposit a thin layer of dielectric material on top of the bare metal. In some examples, lower-capacitance portions 62A, 62B may include titanium nitride with a dielectric layer to reduce the capacitance. In some examples, the dielectric material may also be deposited on a portion of one or both of higher-capacitance portions 64A, 64B to form a lower-capacitance portion 62A, 62B of an electrode 60A, 60B.

In some examples, lower-capacitance portions 62A, 62B may include a first conductive material, and higher-capacitance portions 62A, 62B may include a second conductive material, where the first and second conductive materials are different elements or compounds. One portion may include a titanium, and the other portion may include a metallic material such as platinum, gold, copper, tin, and/or any other suitable conductive material. An electrode may include platinum and a dielectric material covering a portion of the platinum to create a higher-capacitance portion of the electrode. In some examples of this disclosure that employ higher voltages for certain uses of an electrode, a portion of an electrode may include tantalum pentoxide that insulates at lower voltages.

Impedance of electrodes 60A, 60B may be proportional to the surface area of electrodes 60A, 60B, as shown in equation (1):

$$R = \frac{\rho L}{A} \quad (1)$$

$$P = I^2 R = \frac{I^2 \rho L}{A} \quad (2)$$

$$C = \epsilon A / d \quad (3)$$

$$X_c = 1/2\pi f C \quad (4)$$

In equation (1), R represents the resistance, ρ represents the resistivity, L represents the length of a resistive element, and A represents the cross-sectional area of the resistive element. In equation (2), P represents the power dissipated in conducting a signal, and I represents the electrical current of the signal. In equation (3), ε is the dielectric constant of the dielectric layer, A is the area of the capacitor, and d is the thickness of the dielectric. By increasing the effective surface area of electrodes 60A, 60B, lower-capacitance portions 62A, 62B may reduce the resistance and impedance, which may enable higher current capability for TCC transmission and higher received signal strength for TCC reception. If the signal source impedance is relatively large, compared to the load impedance within IMD 15, the received signal may be attenuated, causing a low signal to noise ratio. The load impedance within IMD 15 may be low due to electromagnetic interference suppression capacitors. Lower impedance may also reduce the power dissipation in electrodes 60A, 60B, as shown by equation (2). By increasing the thickness of the dielectric, the capacitance in equation (3) may be reduced. In equation (4), the impedance or capacitive reactance $X_c$ is inversely proportional to the frequency f and the capacitance C. Thus, lower-capacitance portions 62A, 62B may include higher impedance than higher-capacitance portions 64A, 64B. It may be desirable for the capacitive reactance to be negligible compared to the resistance of electrodes 60A, 60B.

For sensing physiological electrical signals, the length of the dipole between electrodes 60A, 60B may be important to the signal quality sensed by electrodes 60A, 60B. Dipole length 72 may represent the effective length between the center of mass of higher-capacitance portion 64A and the center of mass of higher-capacitance portion 64B. For higher-frequency signals such as TCC signals, dipole length 70 may represent the effective length between the center of mass of electrode 60A and the center of mass of electrode 60B. As depicted in FIG. 2, dipole length 72 may be longer than dipole length 70. In some examples, IMD 15 may include dipole length 70 of approximately thirty-four millimeters, dipole length 72 of approximately forty millimeters, and width 74 of approximately eight millimeters. The 15% reduction in dipole length for relatively higher-frequency signals may be compensated by the much larger increase in surface area for the higher-frequency signals.

Although dipole length 70 may be important for communicating via high-frequency signals, current capability and power consumption may be more important considerations in some examples. Current capability may be important with lower-voltage batteries because high impedance may reduce the electrical current through electrodes 60A, 60B. Power consumption may decrease as the surface area of electrodes 60A, 60B is increased. Lower-capacitance portions 64A, 64B being active during transmission of higher-frequency signals may reduce power consumption of ICM 15 by a much larger percentage than power consumption is increased by the resulting reduction in dipole length 70 and the corresponding reduction in transimpedance.

Moreover, the impedance of the tissue surrounding IMD 15 may be important. For example, bone and fat may have a relatively high resistance to electrical signals, while muscle and blood may have a relatively low resistance to electrical signals. At a frequency of eight kHz, the median impedance of tissue in patients may be about nine hundred and forty ohms. If IMD 15 includes a battery voltage of two volts, driving a TCC current of one or two milliamperes into the tissue may require relatively low impedance. A higher impedance may prevent a two-volt battery from driving an adequate TCC current. Thus, in some examples, a reduction in impedance for higher-frequency signals may be desirable.

In one example, each of lower-capacitance portions 62A, 62B may include a surface area of approximately fourteen square millimeters, and each of higher-capacitance portions 64A, 64B may include a surface area of approximately twenty-eight square millimeters. The dipole length and transimpedance may decrease by fifteen percent for transmission of higher-frequency signals, but the impedance may also decrease by sixty-six percent for the higher-frequency signals. Thus, the power efficiency in this example may improve by more than fifty percent:

$$P_{new} = \frac{P_{old}}{(\% \text{ transimpedance})^2 \times (\% \text{ impedance})} = \frac{P_{old}}{0.85^2 \times 3} \approx \frac{P_{old}}{2.17}$$

In some examples, insulative cover 66 and/or can 80 (FIG. 3) may act as an elongate housing that contains processing circuitry, sensing circuitry, and/or communication circuitry. Each of higher-capacitance portions 64A, 64B may be closer to the distal ends of insulative cap 66 than each of lower-capacitance portions 62A, 62B. Likewise, each of lower-capacitance portions 62A, 62B may be closer to antenna 68 than each of higher-capacitance portions 64A, 64B.

FIG. 3 is a conceptual, cross-sectional side-view diagram of the example configuration of ICM 15 of FIG. 2, the cross-section taken along line A-A' of FIG. 2. FIG. 3 depicts each of higher-capacitance portions 64A, 64B as being formed or placed above or on each of lower-capacitance portions 62A, 62B, each of which may be formed or placed above or on top of insulative cover 66. Although shown as a layer above lower-capacitance portions 62A, 62B, higher-capacitance portions 64A, 64B may, in some examples, be formed by treating a portion of a surface of the lower-capacitance portions, e.g., treating a portion of a surface of a bare titanium electrode to form high-surface area titanium-nitride, producing higher-capacitance portion 64.

ICM 15 as depicted in FIG. 3 may include a wafer-scale insulative cover 66 positioned over a can 80 to form the housing of the ICM. Circuitry of ICM 15, e.g., processing circuitry, sensing circuitry, and/or communication circuitry, may be formed on insulative cover 66, e.g., using flip-chip technology. For example, circuitry may be formed on a side of insulative cover 66, and insulative cover 66 may be flipped onto can 80. When flipped and placed onto can 80, the circuitry may be positioned on the bottom side of insulative cover 66 in a gap 84 defined by can 80. The circuitry on insulative cover 66 may be electrically connected to electrodes 60A, 60B through vias 82A, 82B formed through insulative cover 66. Insulative cover 66 may include additional vias not shown in FIG. 3. Insulative cover 66 may be formed of sapphire and/or any other suitable insulating material. Can 80 may be formed from bare titanium or any other suitable material.

In some examples, insulative cover 66 may be sapphire and have a thickness of approximately three hundred micrometers to six hundred micrometers. Can 80 may be titanium and have a thickness of approximately two hundred micrometers to five hundred micrometers. Lower-capacitance portion 62A may be titanium and have a thickness of approximately fifty micrometers to one hundred micrometers. Higher-capacitance portion 64A may be titanium nitride and have a thickness of approximately five hundred nanometers to ten micrometers. Higher-capacitance portion 64A may be more mechanically robust and have a higher capacitance for higher thicknesses. These materials and dimensions are examples only, and other materials and other thicknesses are possible for devices of this disclosure.

FIG. 4 is a conceptual side-view diagram of an IMD 81 including two electrodes 60A and 86. Electrode 60A is described above with respect to FIGS. 2 and 3. IMD 81 may include dielectric material 90 deposited on can 80. Higher-capacitance portion 88 of electrode 86 may be formed or placed on can 80. Higher-capacitance portion 88 of electrode 86 may include similar properties to higher-capacitance portions 64A and 64B. These properties may include capacitance, frequency response (amplitude as a function of frequency), ratios of surface area for higher- and lower-capacitance portions, and any other properties. In one example, can 80 is formed of bare titanium, and higher-capacitance portion 88 is formed by treating a portion of the exposed portion of can 80 to form a titanium-nitride higher-capacitance portion 88. In some examples, material 80 (i.e., "the tub" or "the can") may be connected to a terminal of sensing circuitry and communication circuitry of IMD 81.

FIG. 5 is a conceptual side-view diagram of another example configuration of an IMD 100 including two electrodes 110A, 110B. IMD 100 may include an elongate housing including header 102 and can 104. Header 102 and/or can 104 may house the processing circuitry, sensing circuitry, and/or communication circuitry of IMD 100.

Header 102 may include insulating material such as plastic or any other suitable insulating material. Electrode 110A may include higher-capacitance portion 114A and lower-capacitance portion 112A, and may be attached to header 102. Electrode 110A may be electrically connected to sensing circuitry and communication circuitry within IMD 100. Higher-capacitance portions 114A and 114B may include similar properties to higher-capacitance portions 64A and 64B.

In some examples, can 104 may include conductive material such as bare titanium. Dielectric material 106 may be formed on can 104. The area of can 104 may not be covered with dielectric material 106 may operate as lower-capacitance portion 112B. Higher-capacitance portion 114B may be formed or placed on or over lower-capacitance portion 112B. In some examples, can 104 may include a surface area of approximately seventy square millimeters, while electrode 110A may include a surface area of approximately nine square millimeters. Lower-capacitance portions 112A and 112B may include similar properties to lower-capacitance portions 62A and 62B.

FIG. 6 is a conceptual diagram illustrating an example configuration of an implantable medical lead 121 including electrodes 120A and 120B. Electrodes 120A and 120B may be used for sensing physiological electrical signals, transmitting and/or receiving TCC signals, and/or delivering therapeutic signals to a patient. Electrode 120A may include lower-capacitance portion 122A and higher-capacitance portion 124A, and electrode 120B may include lower-capacitance portion 122B and higher-capacitance portion 124B. Electrodes 120A and 120B may be connected to a lead body 126 which may connect to an IMD or external device. Electrode 120B at distal end 128 of lead body 126 may include at least a portion formed as a fixation structure, e.g., helix, to fix lead 121 to the tissue of the heart and hold the lead in place, or distal end of lead 128 may otherwise include a fixation structure.

Higher-capacitance portions 124A and 124B may be configured to operate as an electrode for communication, sensing, and delivering therapy pulses. Lead 121 may be configured to sense physiological signals and deliver therapeutic signals, e.g., pacing pulses, through higher-capacitance portions 124A and 124B. In some examples, a longer dipole may be desirable, such that the can (not shown in FIG. 6) of a medical device may be used as an electrode. Lead body 126 may be connected to the can of the medical device. A medical device coupled to lead 121 may communicate using TCC through lower-capacitance portions 122A and 122B higher-capacitance portions 124A and 124B of electrodes 120A and 120B, or the lower capacitance and higher capacitance portions of one of the electrodes 120 and the can. Electrode 120B may be similar to electrode 22 in FIG. 1B, and electrode 120A may be a ring electrode, or a coil electrode similar to electrode 42 in FIG. 1B.

For defibrillation, electrode 120B (when configured as a coil electrode 42 (FIG. 1B)) and possibly the housing of IMD 17 in FIG. 1B, may transmit a lower-frequency and higher-voltage signal to the heart tissue. Defibrillation may include relatively higher voltages as compared to other pacing signals and therapy signals. The relatively higher voltages of defibrillation may produce relatively higher electrical currents. A lower defibrillation voltage may be desirable to reduce the need for high-voltage capacitors. A larger electrode surface area may also be desirable for defibrillation to reduce the voltage needed to generate an adequate current for defibrillation.

Figure 7A:
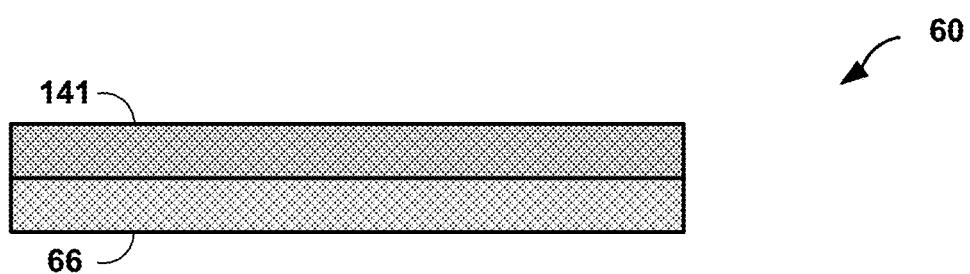
FIGS. 7A-7D are block diagrams illustrating an example technique for manufacturing an electrode including a higher-capacitance portion and a lower-capacitance portion.

FIGS. 7A-7D are conceptual diagrams of an example technique for manufacturing an electrode 60 including a higher-capacitance portion 64 and a lower-capacitance portion 62. The method may begin with insulative cover 66. FIG. 7A depicts conductive material 141 formed on insulative cover 66. Conductive material 141 may include, as examples, bare titanium or titanium dioxide.

Figure 7B:
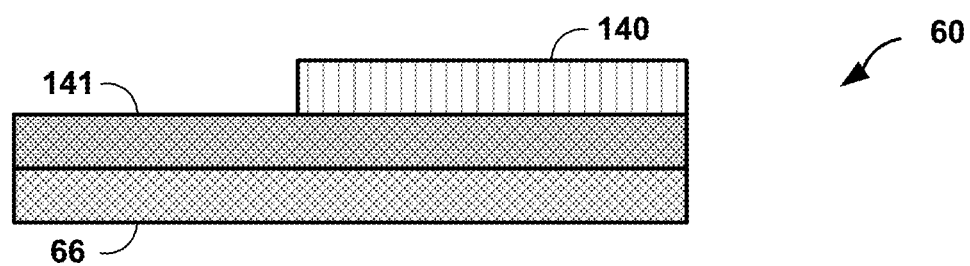
Figure 7C:
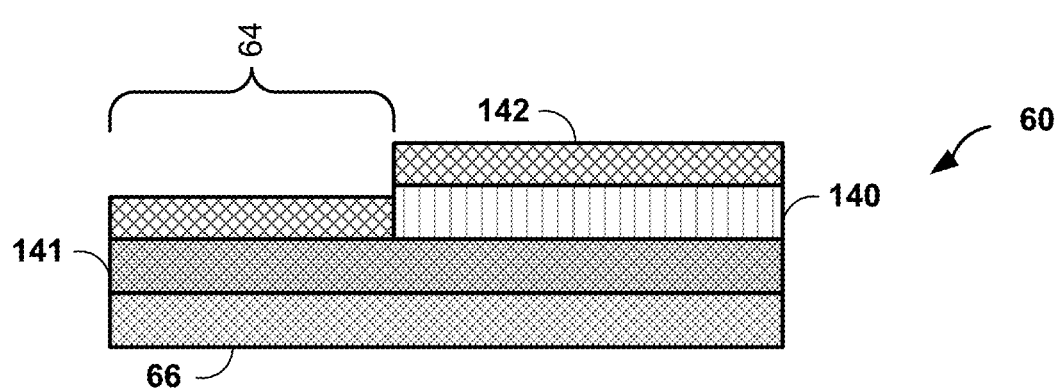
Figure 7D:
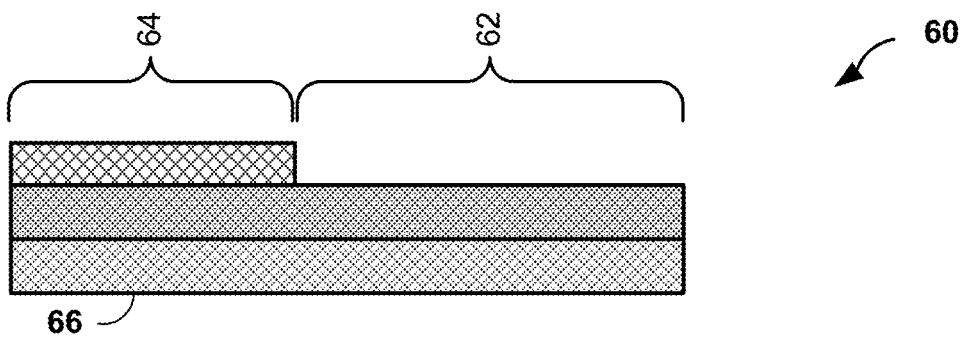

FIG. 7B depicts mask 140 formed on part of conductive material 141. FIG. 7C depicts another material 142 on mask 140 and conductive material 141. Mask 140 may prevent material 142 from contacting some of conductive material 141. The portion of material 142 that contacts conductive material 141 may form higher-capacitance portion 64. Material 142 may include an element or compound, e.g., nitrogen, such that higher-capacitance portion 64 may include a mixture or composition of material 142 and conductive material 141, such as titanium nitride. FIG. 7D depicts the removal of mask 140 and material 142 that was disposed on mask 140, exposing conductive material 141. The exposed portion of conductive material 141 may become lower-capacitance portion 62. The process of FIGS. 7A-7D may be repeated, or performed on two areas of insulative cover 66 substantially simultaneously, to construct a second electrode 60, and thereby construct two electrodes 60A, 60B, e.g., as illustrated in FIGS. 2 and 3.

Figure 8:
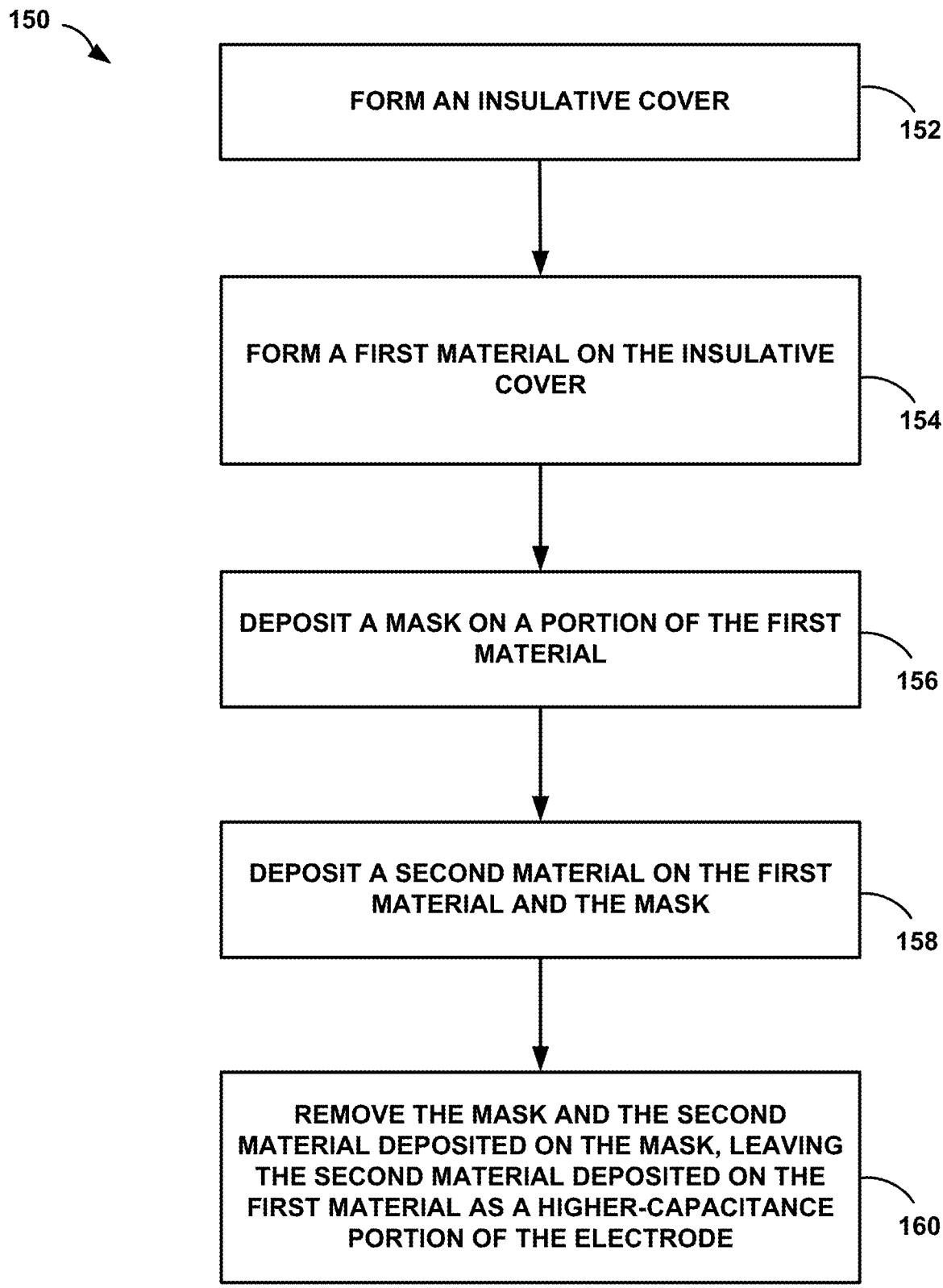
FIG. 8 is a flowchart illustrating an example technique of manufacturing an electrode including a higher-capacitance portion and a lower-capacitance portion.

FIG. 8 is a flowchart illustrating an example technique 150 of manufacturing an electrode including a higher-capacitance portion 64 and a lower-capacitance portion 62. Technique 150 may be implemented in the construction of any one of the implantable medical devices (IMDs) discussed above because each one of the IMDs is configured to include an electrode including a higher-capacitance portion and a lower-capacitance portion. The technique of FIG. 8 may be described in the context of electrode 60 of FIGS. 7A-7D.

The technique of FIG. 8 may include forming insulative cover 66, which may include sapphire in some examples (152). Insulative cover 66 may include circuitry attached to one side. The technique of FIG. 8 may also include forming first material 141 on insulative cover 66 (154). First material 141 may include bare titanium or another conductive material. The technique of FIG. 8 may also include depositing mask 140 on a portion of first material 141 (156). The technique of FIG. 8 may also include depositing second material 142 on first material 141 and mask 140 (158). Mask 140 may block material 142 from contacting all of first material 141. The technique of FIG. 8 may also include removing mask 140 and material 142 that is deposited on mask 140, leaving the second material deposited on first material 141 as higher-capacitance portion 64A on electrode 60A (160).

Figure 9A:
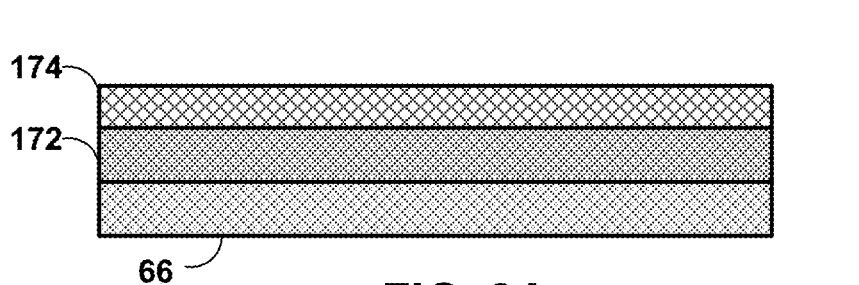
FIGS. 9A-9D are block diagrams illustrating an example technique for manufacturing an electrode using dielectric material.

FIGS. 9A-9D are block diagrams of a method of manufacturing an electrode 170 using dielectric material 178. The method may begin with insulative cover 66. FIG. 9A depicts conductive material 172 formed on insulative cover 66. Conductive material 172 may include, as examples, bare titanium or any other conductive material in some examples. FIG. 9A depicts another material 174 formed on conductive material 172. Material 174 may be formed by treating conductive material 172 with an element or compound, e.g., nitrogen, on conductive material 172, such that titanium nitride or another material forms with a higher capacitance.

Figure 9B:
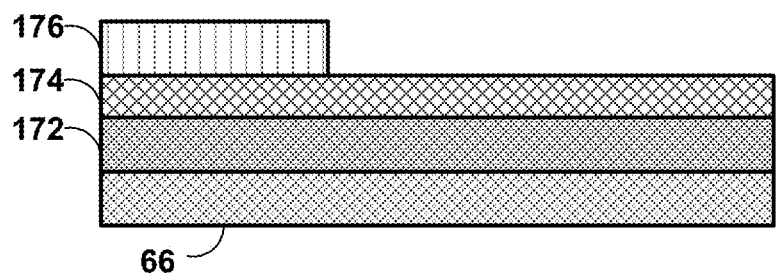
Figure 9C:
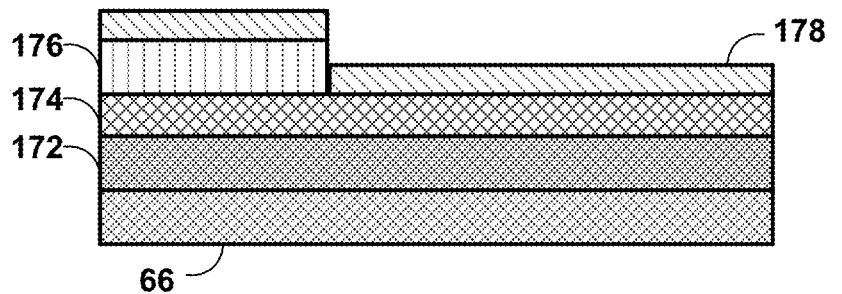
Figure 9D:
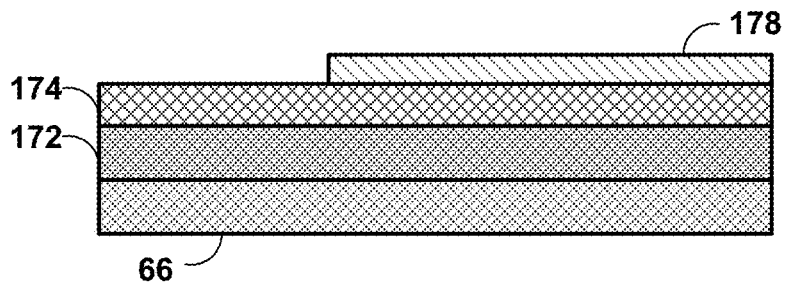

FIG. 9B depicts mask 176 deposited on a portion of material 174. FIG. 9C depicts dielectric material 178 deposited on material 174 and on mask 176. Mask 176 may block dielectric material 178 from attaching to a portion of material 174. Dielectric material 178 may include any suitable dielectric material, such as parylene. FIG. 9D depicts the removal of mask 176 and dielectric material 178 that was attached to mask 176, exposing material 174 to form a higher-capacitance portion. The portion of material 174 that is covered by dielectric material 178 may operate as a lower-capacitance portion.

Figure 10:
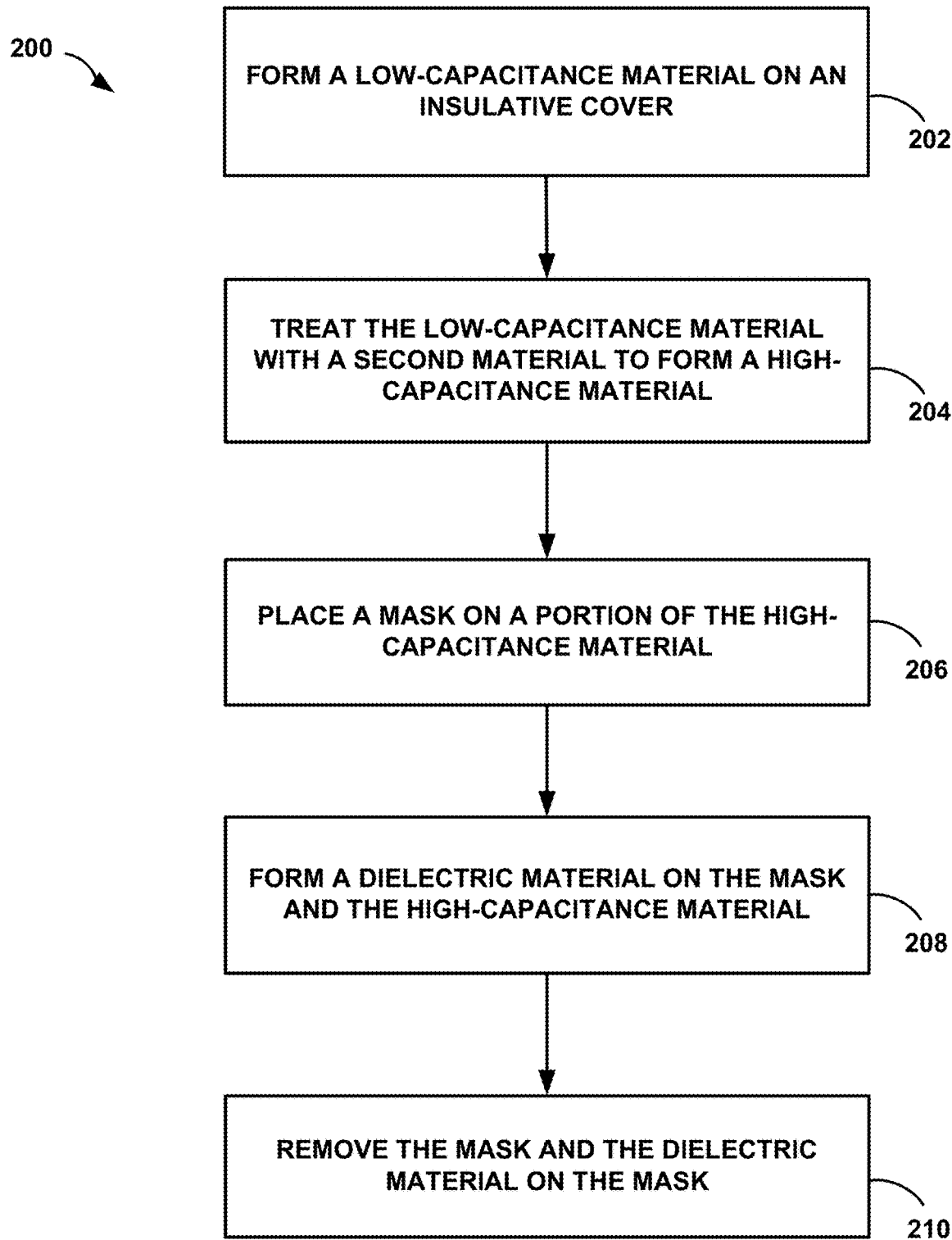
FIG. 10 is a flowchart illustrating an example technique of manufacturing an electrode using dielectric material.

FIG. 10 is a flowchart illustrating an example technique 200 of manufacturing an electrode using dielectric material. Technique 200 may be implemented by any one of the implantable medical devices (IMDs) discussed above because each one of the IMDs is configured to include at least one electrode.

The technique of FIG. 10 includes forming conductive material 172 on insulative material 66 (202). Conductive material 172 may include a conductive material with low capacitance such as titanium or titanium oxide. The technique of FIG. 10 further includes treating conductive material 172 with a second material, such as nitrogen, to form material 174 (204). The technique of FIG. 10 further includes placing mask 176 on a portion of material 174 (206). The technique of FIG. 10 further includes forming dielectric material 178 on mask 176 and material 174 (208). The technique of FIG. 10 further includes removing mask 176 and the portion of dielectric material 178 on mask 176 (210). The remaining dielectric material 178 may lower the capacitance of the portion of material 174 that dielectric material 178 covers.

The capacitance per unit area of materials used for electrodes may be adjusted by changing the surface finish of the electrode. For example, the capacitance of a material such as anodized titanium may be modified by controlling the thickness of an oxide layer. The thickness of the oxide layer may be controlled by changing the voltage, current, time, and/or solution used in the anodizing process.

Figure 11:
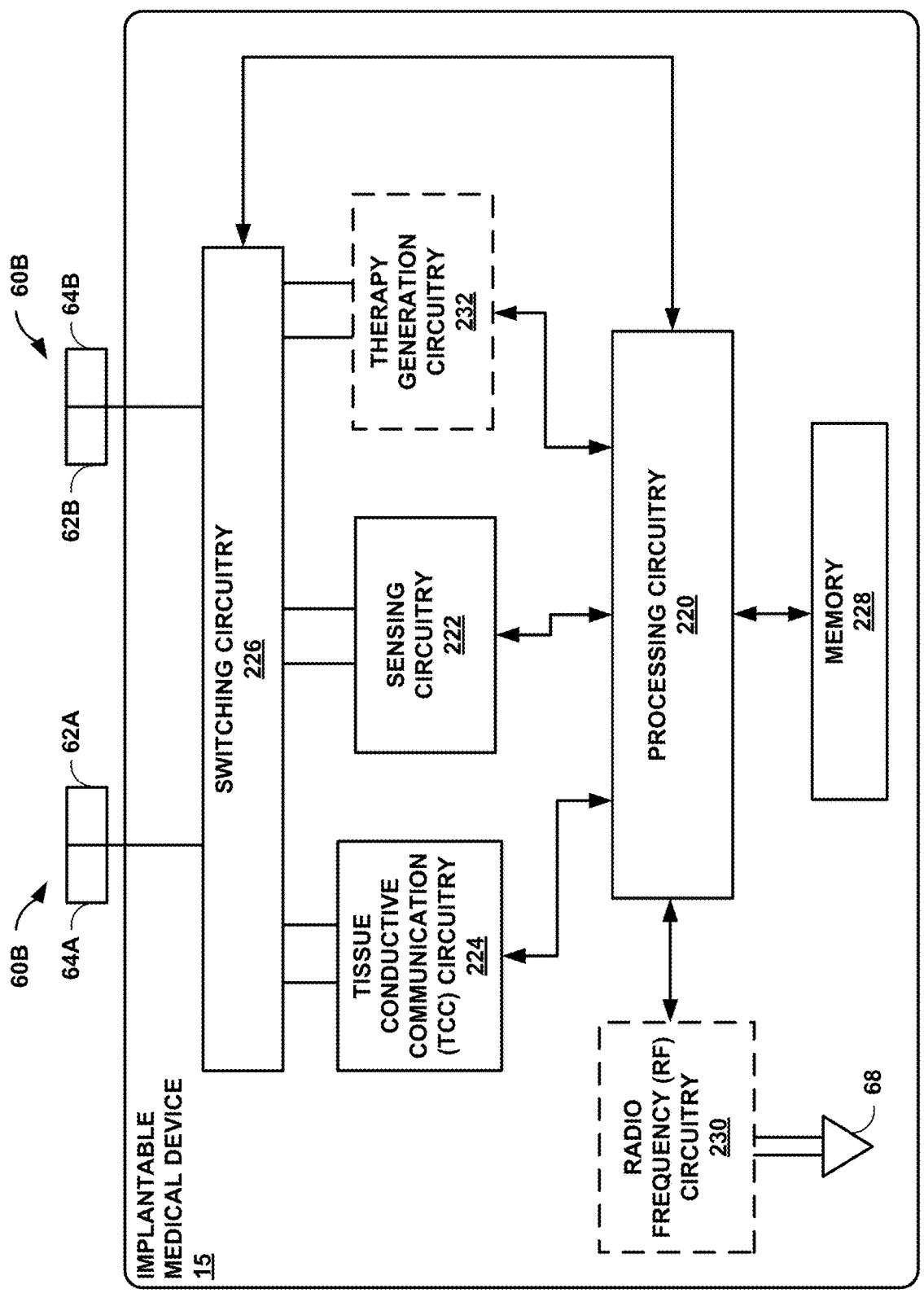
FIG. 11 is a block diagram of an example configuration of an implantable medical device including two electrodes.

FIG. 11 is a block diagram of an example configuration of an IMD 15 including two electrodes 60A, 60B. IMD 15 may include processing circuitry 220 for controlling sensing circuitry 222, TCC circuitry 224, switching circuitry 226, memory 228, optional RF circuitry 230, and optional therapy generation circuitry 232. Switching circuitry 226 may include one or more switches, such as metal-oxide-semiconductor field-effect transistors (MOSFETs) or bipolar transistors. Processing circuitry 220 may control switching circuitry 226 to connect electrodes 60A, 60B to sensing circuitry 222 to sense a physiological electrical signal. IMD 15 may sense the physiological electrical signal, which may have a relatively lower frequency content through higher-capacitance portions 64A, 64B of electrodes 60A, 60B.

Moreover, processing circuitry 220 may control switching circuitry 226 to connect electrodes 60A, 60B to TCC circuitry 224 to transmit or receive TCC signals. Because TCC signals may have a relatively higher frequency content, e.g., than physiological signals or therapy signal, both higher-capacitance portions 64A, 64B and lower-capacitance portions 62A, 62B of electrodes 60A, 60B may be active during transmission and receipt of TCC signals. In some examples, processing circuitry 220 may control switching circuitry 226 to connect electrodes 60A, 60B to therapy generation circuitry 232 to deliver a therapy pulse, such as a pacing pulse to the heart. IMD 15 may deliver the therapy pulse, which may have a relatively lower frequency content, through higher-capacitance portions 64A, 64B. Lower-capacitance portions 62A and 62B may be configured to not deliver the therapy pulse because lower-capacitance portions 62A and 62B may have a relatively high impedance for lower-frequency therapy pulses. Lower-capacitance portions 62A and 62B may conduct lower-frequency therapy pulses, but the amplitude of the current through lower-capacitance portions 62A and 62B may be much lower than the amplitude of the current through higher-capacitance portions 64A, 64B. As a result, the electrical current through higher-capacitance portions 64A, 64B may be at least approximately ten, twenty, or one hundred times higher than the electrical current through lower-capacitance portions 62A and 62B. Therapy generation circuitry 232 and/or processing circuitry 220 may control the frequency, amplitude, and other characteristics of the therapy pulses. Therapy generation circuitry 232 may deliver the therapy pulses to electrodes 60A, 60B when switching circuitry 226 connects therapy generation circuitry 232 to electrodes 60A, 60B.

Processing circuitry 220 may control switching circuitry 226 by sending control signals to the control terminals of one or more switches of switching circuitry 226. The control signals may control whether the switches of switching circuitry 226 conduct electricity between the load terminals of the switches. If switching circuitry 226 includes MOSFET switches, the control terminals may include gate terminals, and the load terminals may include drain terminals and source terminals.

Figure 12:
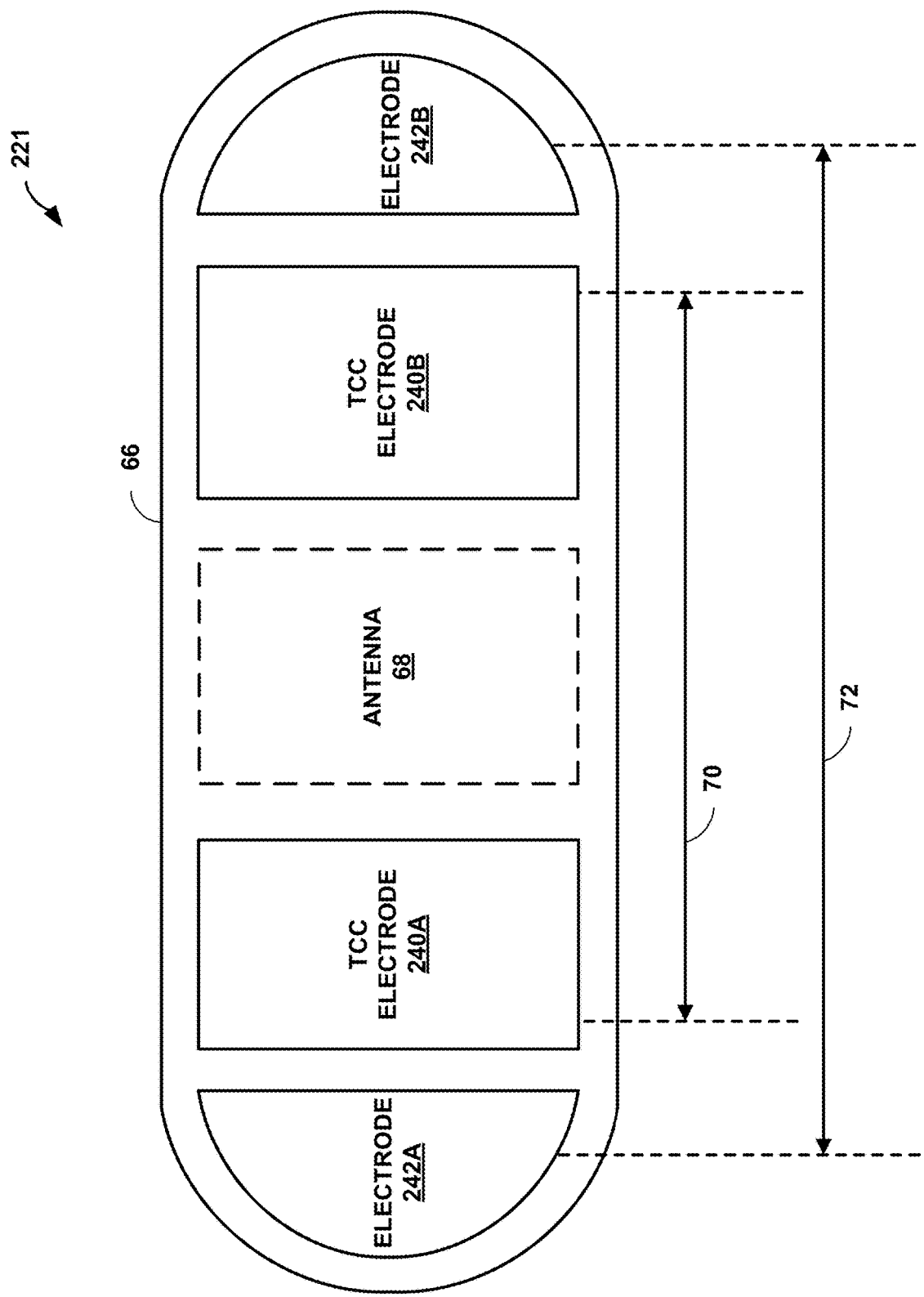
FIG. 12 is a top-view diagram of an example configuration of an implantable medical device including four electrodes and an antenna.

FIG. 12 is a conceptual top-view diagram of an example configuration of an implantable medical device 221 including four electrodes 240A, 240B, 242A, 242B and an antenna 68. IMD 221 may include switching circuitry configured to connect some or all of electrodes 240A, 240B, 242A, 242B to sensing circuitry and/or communication circuitry of IMD 221. The switching circuitry is configured to connect the sensing circuitry to electrodes 242A, 242B, e.g., and not to TCC electrodes 240A, 240B, to sense a physiological electrical signal through electrodes 242A, 242B.

Dipole length 72 between the centers of electrodes 242A, 242B may be longer than dipole length 70 between the centers of the combination of electrodes 240A, 242A and the combination of electrodes 240B, 242B. Dipole length 72 may provide a larger transimpedance and signal amplitude than dipole length 70 for sensing physiological electrical signal. In some examples, all of electrodes 240A, 240B, 242A, 242B may include the same material, such as titanium nitride. To increase the dipole length, the processing circuitry of IMD 221 may control the switching circuitry to switch off electrodes 240A, 240B when sensing or transmitting low-frequency signals.

To increase the surface area for transmitting or receiving high-frequency signals, the processing circuitry may control the switching circuitry to switch on all of electrodes 240A, 240B, 242A, 242B, with electrodes 240A and 242A acting as one effective electrode, and electrodes 240B and 242B acting as another effective electrode. The communication circuitry may be configured to transmit or receive a TCC signal through electrodes 240A and 242A, and electrodes 240B and 242B.

In some examples, IMD 221 may include three electrodes for TCC and sensing. The battery of IMD 221 may be positioned near a single electrode in place of electrodes 240A, 242A. The single electrode may be used for both TCC and sensing signals. A three-electrode version of IMD 221 may include electrodes 240B and 242B on an opposite end from the single electrode to increase the dipole distance for sensing and lower the impedance for TCC.

Figure 13:
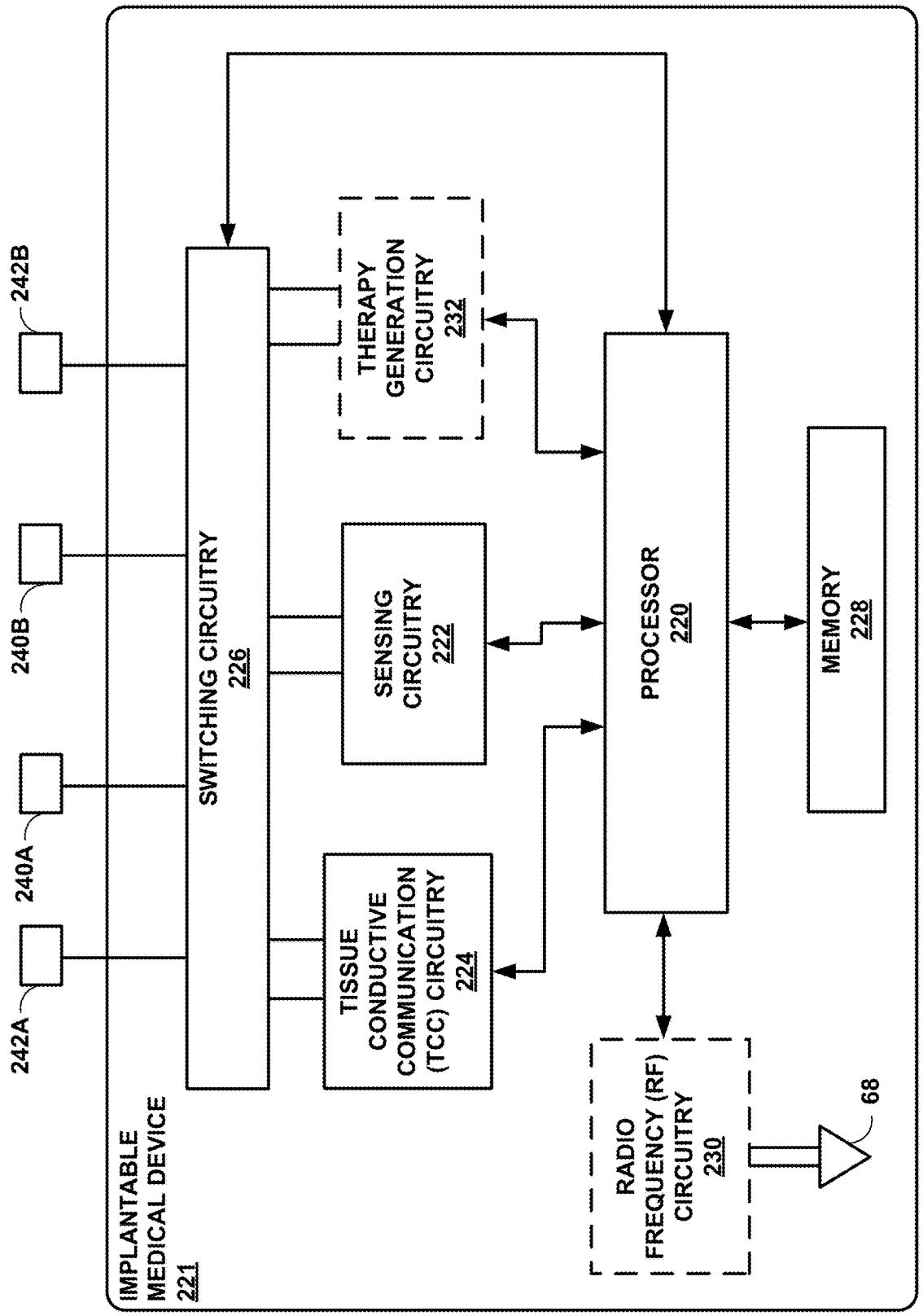
FIG. 13 is a block diagram illustrating an example configuration of an implantable medical device including four electrodes.

FIG. 13 is a block diagram illustrating an example configuration of an implantable medical device 221 including four electrodes 240A, 240B, 242A, 242B. Switching circuitry 226, as controlled by processing circuitry 220 may be configured to connect electrodes 242A, 242B to sensing circuitry 222 to sense physiological electrical signals. Switching circuitry 226 may include one or more switches, such as metal-oxide-semiconductor field-effect transistors (MOSFETs) or bipolar transistors. Switching circuitry 226 may be configured to connect electrodes 240A, 240B, 242A, 242B to transmit or receive TCC signals.

In some examples, processing circuitry 220 may control switching circuitry 226 to connect electrodes 242A, 242B to therapy generation circuitry 232 to deliver a therapy pulse, such as a pacing pulse to the heart. In some examples, electrodes 242A, 242B may have a higher capacitance than electrodes 240A, 240B. IMD 221 may deliver the therapy pulse, which may have a relatively lower frequency content, through electrodes 242A, 242B. Therapy generation circuitry 232 and/or processing circuitry 220 may control the frequency, amplitude, and other characteristics of the therapy pulses. Therapy generation circuitry 232 may deliver the therapy pulses to electrodes 242A, 242B when switching circuitry 226 connects therapy generation circuitry 232 to electrodes 242A, 242B.

Processing circuitry 220 may control switching circuitry 226 by sending control signals to the control terminals of one or more switches of switching circuitry 226. The control signals may control whether the switches of switching circuitry 226 conduct electricity between the load terminals of the switches. If switching circuitry 226 includes MOSFET switches, the control terminals may include gate terminals, and the load terminals may include drain terminals and source terminals.

Figure 14:
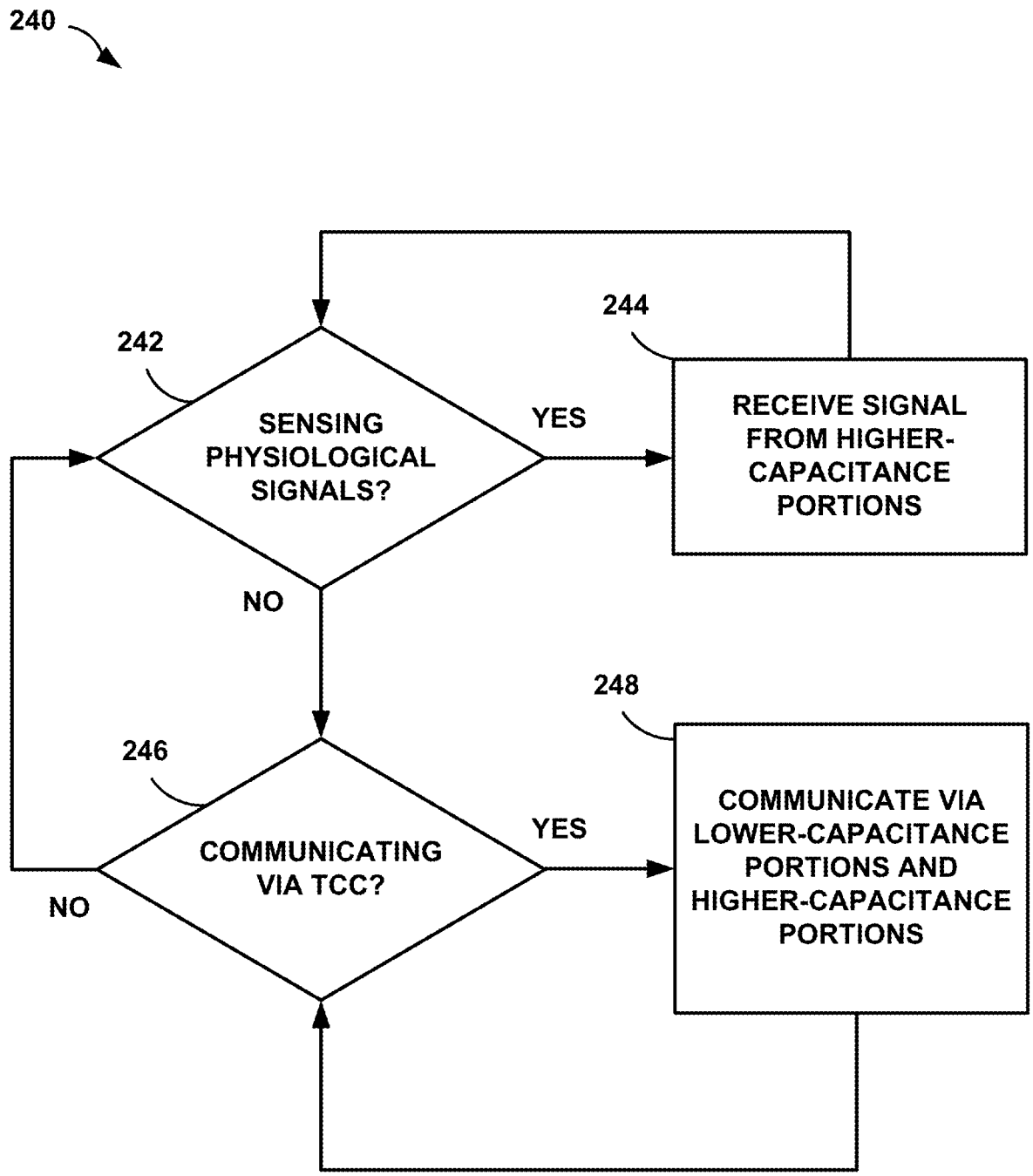
FIG. 14 is a flowchart illustrating an example technique of operating an implantable medical device including two electrodes.

FIG. 14 is a flowchart illustrating an example technique 240 of operating an implantable medical device 15 including two electrodes 60A, 60B. If IMD 15 is sensing physiological signals (242), IMD 15 may receive the physiological signals from higher-capacitance portions 64A, 64B of electrodes 60A, 60B (244). If IMD 15 is communicating via TCC signals (246), both lower-capacitance portions 62A, 62B and higher-capacitance portions 64A, 64B of electrodes 60A, 60B may be active (248).

Figure 15:
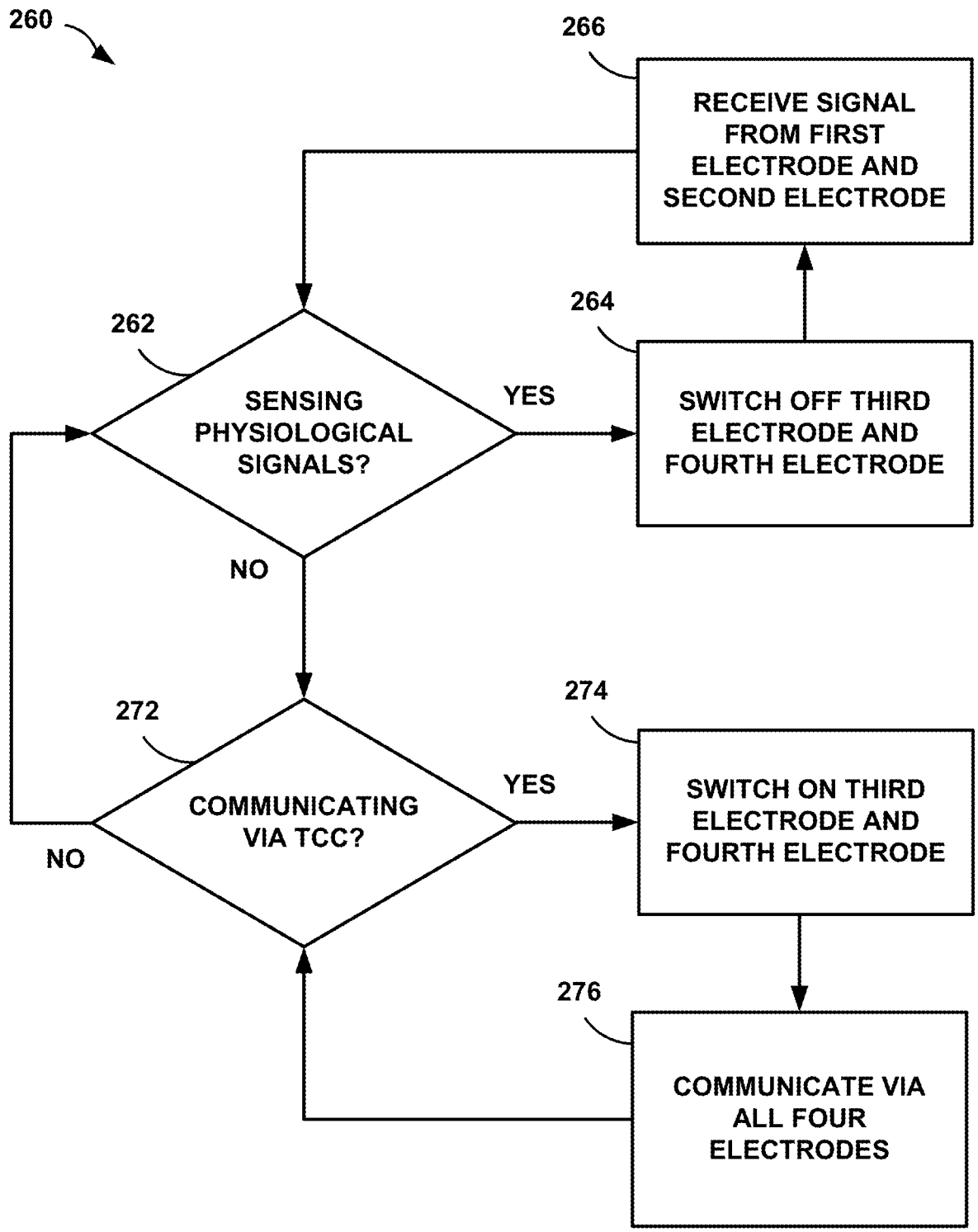
FIG. 15 is a flowchart illustrating an example technique of operating an implantable medical device including four electrodes.

FIG. 15 is a flowchart illustrating an example technique 260 of operating an implantable medical device 221 including four electrodes 240A, 240B, 242A, 242B. If IMD 221 is sensing physiological signals (262), switching circuitry 226 may switch off electrodes 240A, 240B (264). Switching circuitry 226 may switch off electrodes 240A, 240B by disconnecting electrodes 240A, 240B from sensing circuitry 222 and connecting electrodes 242A, 242B to sensing circuitry 222. Sensing circuitry 222 may receive a physiological signal from electrodes 242A, 242B (266).

If IMD 221 is communicating via TCC signals (272), switching circuitry 226 may switch on electrodes 240A, 240B, 242A, and 242B (274). IMD 221 may communicate via TCC signals by receiving signals from a control module. Switching circuitry 226 may switch on electrodes 240A, 240B, 242A, and 242B for communicating TCC signals by connecting electrodes 240A, 242A and electrodes 240B, 242B to respective nodes (e.g., input or output) of TCC communication circuitry 224. TCC communication circuitry 224 may transmit and/or receive TCC signals via the connected electrodes 240A, 240B, 242A, 242B (276). In some examples, TCC communication circuitry 224 may transmit and/or receive TCC signals via at least electrodes 240A, 240B.

Figure 16:
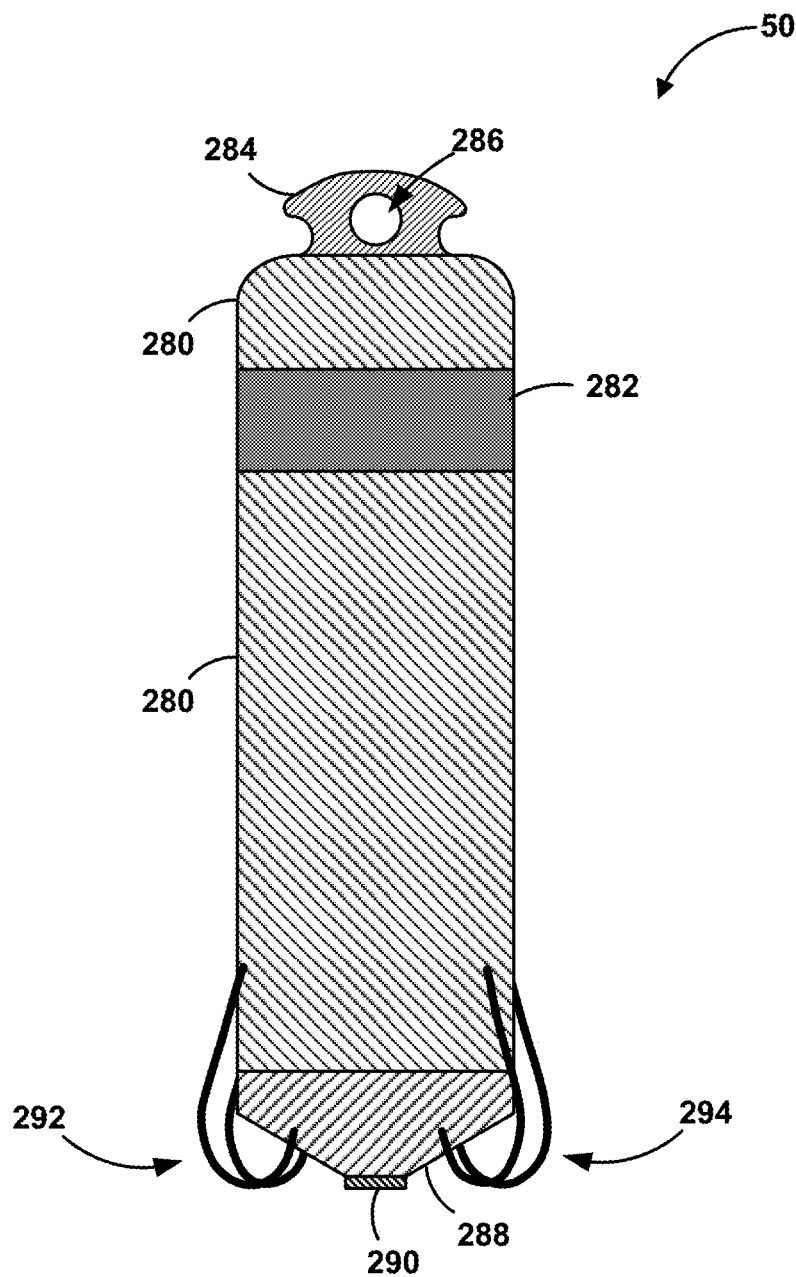
FIG. 16 is a conceptual diagram of an implantable medical device including a tip electrode.
Figure 18:
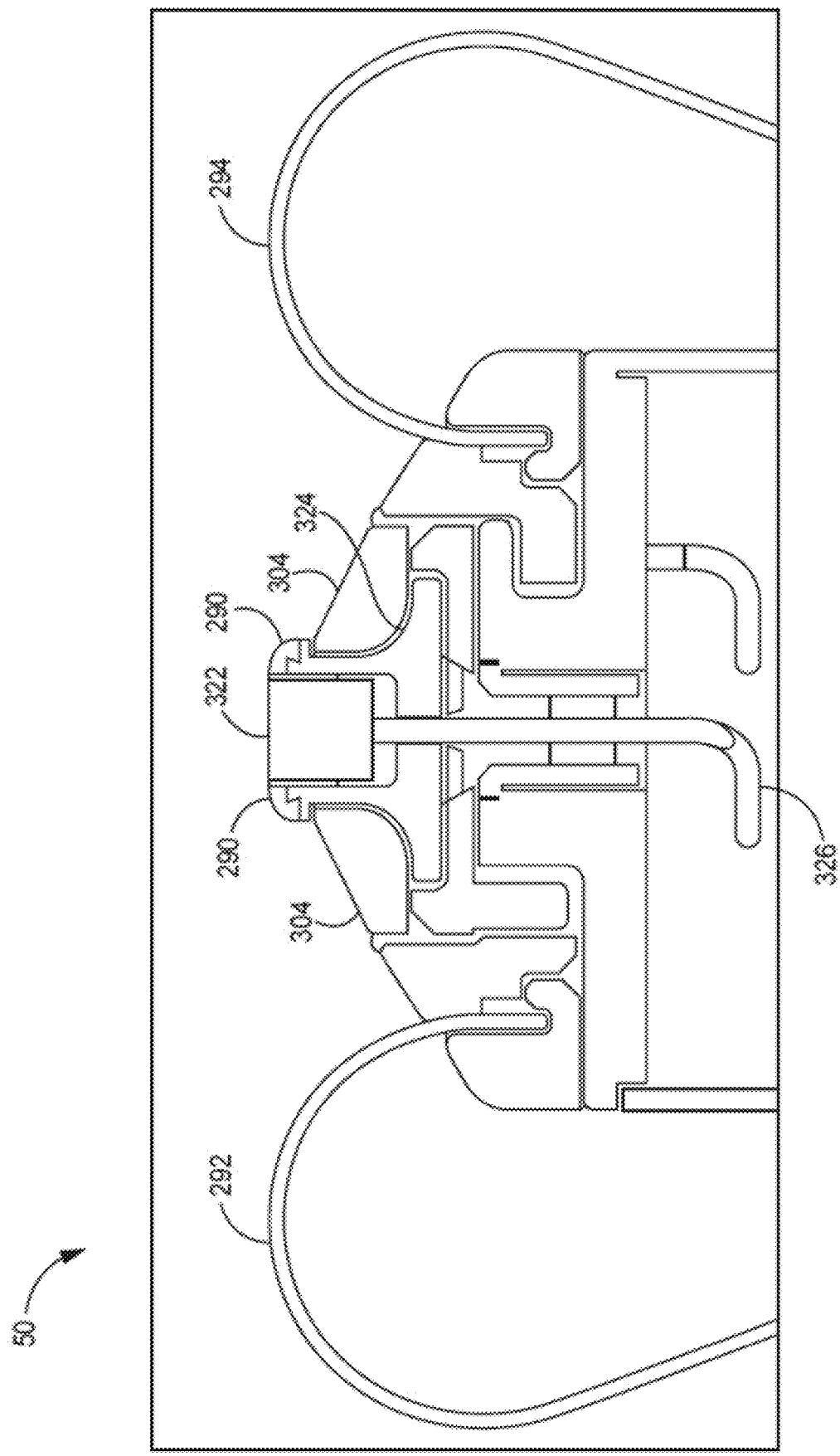
FIG. 18 is a cross-section diagram of an example configuration of a distal portion of an implantable medical device having a tip electrode.

FIG. 16 is a diagram of an implantable medical device 50 including a tip electrode 290. IPD 50 may be configured to be implanted in the left ventricle of the heart of a patient, as depicted in FIG. 1B. As shown in FIG. 16, IPD 50 includes case 280, cap 288, electrode 290, electrode 282, fixation mechanisms 292, flange 284, and opening 286. Together, case 280 and cap 288 may be considered the housing of IPD 50. In this manner, case 280 may form a hermetical seal around the various electrical components, e.g., circuitry, within IPD 50. Cap 288 may hold in place the tip electrode assembly and the tine assembly, as shown in FIG. 18. Case 280 may enclose substantially all of the electrical components and create the hermetically sealed housing of IPD 50. Although IPD 50 is generally described as including one or more electrodes, IPD 50 may typically include at least two electrodes (e.g., electrodes 282 and 290) to deliver an electrical signal (e.g., therapy such as cardiac pacing) and/or provide at least one sensing vector.

Electrodes 282 and 290 are carried on case 280 and cap 288, respectively. In this manner, electrodes 282 and 290 may be considered leadless electrodes. In the example of FIG. 16, electrode 290 is disposed on the exterior surface of cap 288. Electrode 290 may be a circular electrode positioned to contact cardiac tissue upon implantation. Electrode 282 may be a ring or cylindrical electrode disposed on the exterior surface of case 280. Although not depicted in FIGS. 16-17B, electrode 282 may include a higher-capacitance portion and a lower-capacitance portion. Both case 280 and cap 288 may be electrically insulating.

Electrode 290 may be used as a cathode and electrode 282 may be used as an anode, or vice versa, for delivering cardiac pacing such as bradycardia pacing, CRT, ATP, or post-shock pacing. However, electrodes 282 and 290 may be used in any stimulation configuration. In addition, electrodes 282 and 290 may be used to detect intrinsic electrical signals from cardiac muscle. Tip electrode 290 may be configured to contact cardiac tissue such as an interior wall of the left ventricle, the right ventricle, or the right atrium. Tip electrode 290 may be configured to contact cardiac tissue epicardially or intracardially.

Fixation mechanisms 292 may attach IPD 50 to cardiac tissue. Fixation mechanisms 292 may be active fixation tines, screws, clamps, adhesive members, or any other mechanisms for attaching a device to tissue. As shown in the example of FIG. 16, fixation mechanisms 292 may be constructed of a memory material, such as a shape memory alloy (e.g., nickel titanium), that retains a preformed shape. During implantation, fixation mechanisms 292 may be flexed forward to pierce tissue and allowed to flex back towards case 280. In this manner, fixation mechanisms 292 may be embedded within the target tissue.

Flange 294 may be provided on one end of case 280 to enable tethering or extraction of IPD 50. For example, a suture or other device may be inserted around flange 294 and/or through opening 296 and attached to tissue. In this manner, flange 294 may provide a secondary attachment structure to tether or retain IPD 50 within the heart if fixation mechanisms 292 fail. Flange 294 and/or opening 296 may also be used to extract IPD 50 once the 1 MB needs to be explanted (or removed) from the patient if such action is deemed necessary.

Figure 17A:
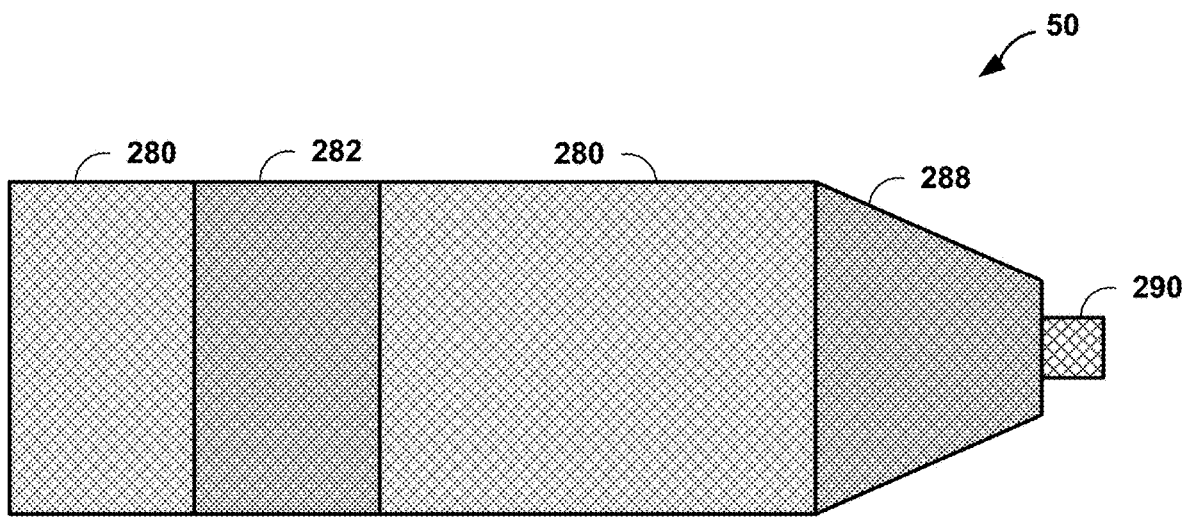
FIGS. 17A-17B are conceptual diagrams of an implantable medical device including a tip electrode.
Figure 17B:
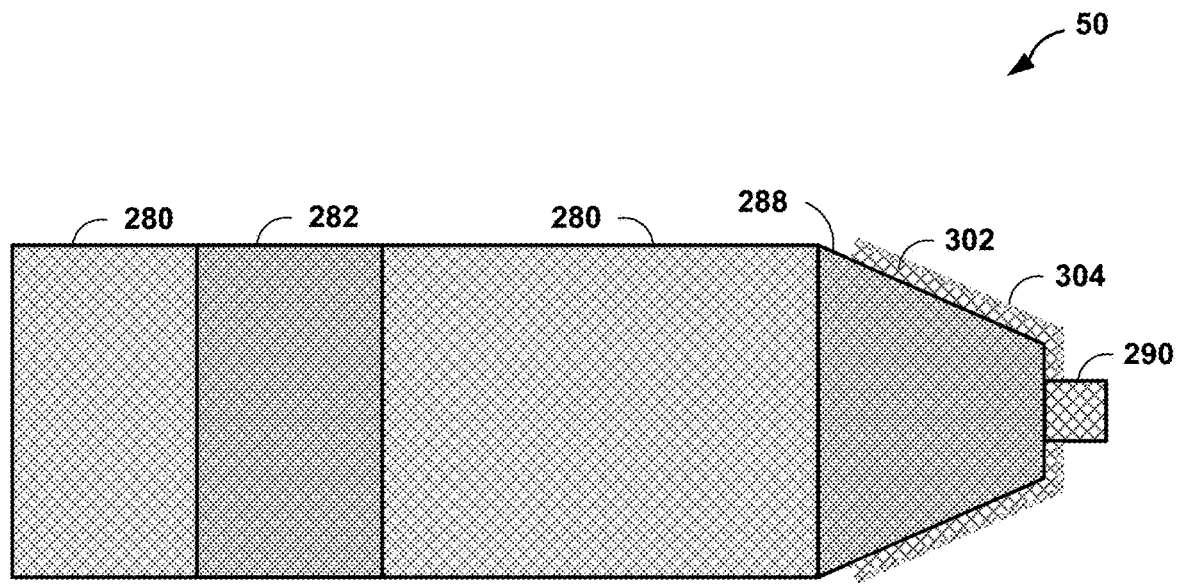

IPD 50 is one example of a pacing device configured to include one or more electrodes according to this disclosure. However, other implantable medical devices may be configured to include one or more electrodes similar to those described with respect to IPD 50. FIGS. 17A-17B are conceptual diagrams of an implantable medical device 50 including a tip electrode 290. FIG. 17A depicts an example that is similar to IPD 50 in FIG. 16, while FIG. 17B depicts IPD 50 including conductive layer 302 adjacent to tip electrode and thin insulating overcap 304 deposited over conductive layer 302. IPD 50 in FIG. 17A may be a depiction of cap 288 and tip electrode 290 before conductive layer 302 and overcap 304 are added. Tip electrode 290 may have a relatively higher capacitance than conductive layer 302 as covered by insulating overcap 304. Consequently, tip electrode 290 may act as a higher-capacitance portion for delivering or sensing lower frequency signals, e.g., pacing signals or physiological signals, while the combination of tip electrode 290 and conductive layer 302 as covered by insulating overcap 304 may provide an increased surface area for transmission or receipt of high-frequency signals, e.g., TCC signals, but generally not conduct lower frequency signals. Moreover, material may be applied to electrode 282 to create a lower-capacitance portion and a higher-capacitance portion.

IPD 50 may engage in one-way or two-way communication with other devices, such as IMD 15 or another IPD 50. IPD 50 may receive commands and data from IMD 15, and IPD 50 may transmit data to IMD 15 or external device 14B. When IPD 50 is transmitting signals, a larger electrode with lower impedance may be desirable to enable higher current capabilities during TCC transmission and higher received signal strength during TCC reception. In some examples, lower impedance may also reduce power dissipation and consequently increase the battery life of IPD 50. Larger surface area of an electrode may also reduce the likelihood that a TCC transmission from IPD 50 will inadvertently cause tissue stimulation.

In some examples, tip electrode 290 may include a surface area of approximately two square millimeters. In experiments using a similar tip electrode in several patients, the impedance had a mean value of six hundred and eighteen ohms. To reduce the effective impedance at high frequencies without significantly increasing the pacing current at low frequencies, conductive layer 302 may provide an impedance in parallel with tip electrode 290. If the capacitance of conductive layer 302 is too high, the pacing current at low frequencies may increase significantly. If the capacitance of conductive layer 302 is too low, conductive layer 302 may not adequately reduce the impedance at high frequencies.

In some examples, the charge delivered to tip electrode 290 for a pacing current may be estimated at three hundred and ninety nanocoulombs, based on a voltage of one volt, an average impedance of six hundred and twenty ohms, and a time period of two hundred and forty microseconds. Adding conductive layer 302 with overcap 304 may increase the pacing current. For an increase in the pacing current of ten percent, the additional charge would be thirty-nine nanocoulombs. Thus, an estimate of the maximum capacitance is forty nanofarads for some pacing devices. An estimate of the minimum capacitance may be obtained using fifty kHz as a low-end frequency for TCC communication and one thousand ohms as a high-end impedance:

$$C_{max} = \frac{Q}{V} = \frac{39\,nC}{1\,V} \approx 40\text{ nF}$$

$$C_{min} = \frac{1}{2\pi f X_c} = \frac{1}{2\pi f(50\text{ kHz})(1\,k\Omega)} \approx 3\text{ nF}$$

FIG. 18 is a cross-section diagram of an example configuration of a distal portion of an implantable medical device having a tip electrode 290. Tip electrode 290 may include a cylinder surrounding steroid eluting silicone plug 322. Metal cylinder 324 may be positioned underneath tip electrode 290. Metal cylinder 324 may include a flat base to hold silicone plug 322 in place, support tip electrode 290, and provide a connection to feedthrough pin 326. Insulating overcap 304 may include a silicone rubber piece that wraps around metal cylinder 324 to insulate the metallic pieces within IPD 50 from external fluids. Insulating overcap 304 may be adhered to other components of IPD 50 by a silicone medical adhesive.

Insulating overcap 304 may include a surface area of eight square millimeters. In some examples according to this disclosure, insulating overcap 304 may be replaced by an insulated metal piece with a similar surface area and a capacitance of approximately ten nanofarads, e.g., conductive layer 302 covered by insulating overcap 304 as depicted in FIG. 17B. In some examples, tip electrode 290 may include an impedance of one thousand ohms, and overcap 304 may include an impedance of three hundred ohms in series with ten nanofarads. The combined impedance of tip electrode 290 and overcap 304 may be three hundred and thirty ohms, two hundred and sixty ohms, and two hundred and forty ohms at fifty kHz, one hundred kHz, and two hundred kHz, respectively. Thus, overcap 304 may reduce impedance for high-frequency signals. However, the increase in pacing current may be relatively low, such as five nanoamperes or two-and-one-half percent.

To design overcap 304 and other components of IPD 50 as a lower-capacitance portion of tip electrode 290, several materials may be used. Titanium nitride or bare titanium may provide a relatively high capacitance. A ten-micrometer layer of parylene for overcap 304 may result in a capacitance of approximately twenty-one picofarads, which may be too low for TCC signals. Anodized titanium may include a capacitance of five nanofarads per square millimeter at certain thicknesses, such as two hundred nanometers.

Various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, electrical stimulators, or other devices. The term "processor" or "processing circuitry" may generally refer to any of the foregoing logic circuitry, alone or in combination with other logic circuitry, or any other equivalent circuitry.

In one or more examples, the functions described in this disclosure may be implemented in hardware, software, firmware, or any combination thereof. If implemented in software, the functions may be stored on, as one or more instructions or code, a computer-readable medium and executed by a hardware-based processing unit. Computer-readable media may include computer-readable storage media forming a tangible, non-transitory medium. Instructions may be executed by one or more processors, such as one or more DSPs, ASICs, FPGAs, general purpose microprocessors, or other equivalent integrated or discrete logic circuitry. Accordingly, the term "processor," as used herein may refer to one or more of any of the foregoing structure or any other structure suitable for implementation of the techniques described herein.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

The following numbered examples demonstrate one or more aspects of the disclosure.

Example 1

An implantable medical device comprising a plurality of electrodes, sensing circuitry configured to sense a physiological electrical signal via the plurality of electrodes, and communication circuitry configured to transmit and/or receive a tissue conductance communication signal via the plurality of electrodes, wherein at least one electrode of the plurality of electrodes comprises a lower-capacitance portion and a higher-capacitance portion.

Example 2

The implantable medical device of example 1, wherein the plurality of electrodes comprises a first electrode including a first lower-capacitance portion and a first higher-capacitance portion; and a second electrode including a second lower-capacitance portion and a second higher-capacitance portion.

Example 3

The implantable medical device of examples 1-2 or any combinations thereof, further comprising an elongate housing that contains the sensing circuitry and the communication circuitry, the elongate housing including a first end and second end opposite the first end, wherein the first electrode is positioned on the elongate housing proximate the first end; the second electrode is positioned on the elongate housing proximate the second end; the first higher-capacitance portion is closer to the first end than the first lower-capacitance portion; and the second higher-capacitance portion is closer to the second end than the second lower-capacitance portion.

Example 4

The implantable medical device of examples 1-3 or any combinations thereof, further comprising an elongate housing and an antenna on or within the elongate housing, wherein the antenna is disposed between the first electrode and the second electrode; the first lower-capacitance portion is positioned closer to the antenna than the first higher-capacitance portion; and the second lower-capacitance portion is positioned closer to the antenna than the second higher-capacitance portion.

Example 5

The implantable medical device of examples 1-4 or any combinations thereof, wherein a distance between a center of the first electrode and a center of the second electrode is less than a distance between a center of the first higher-capacitance portion and a center of the second higher-capacitance portion.

Example 6

The implantable medical device of examples 1-5 or any combinations thereof, wherein the lower-capacitance portion includes titanium or titanium dioxide; and the higher-capacitance portion includes titanium nitride.

Example 7

The implantable medical device of examples 1-6 or any combinations thereof, wherein the lower-capacitance portion is configured to transmit or receive TCC signals; and the higher-capacitance portion is configured to sense the physiological electrical signal and transmit or receive TCC signals.

Example 8

The implantable medical device of examples 1-7 or any combinations thereof, further comprising signal generation circuitry configured to deliver a therapy pulse via the at least one electrode, wherein the higher-capacitance portion is configured to deliver the therapy pulse and the lower-capacitance portion is configured to not deliver the therapy pulse.

Example 9

The implantable medical device of examples 1-8 or any combinations thereof, wherein the lower-capacitance portion is a larger percentage of a surface area of the at least one electrode than the higher-capacitance portion.

Example 10

The implantable medical device of examples 1-9 or any combinations thereof, wherein the lower-capacitance portion includes a capacitance of less than approximately forty nanofarads and greater than approximately three nanofarads; and the higher-capacitance portion includes a capacitance of greater than approximately two hundred nanofarads.

Example 11

The implantable medical device of examples 1-10 or any combinations thereof, further comprising a dielectric material at least partially covering the lower-capacitance portion and/or the higher capacitance portion.

Example 12

The implantable medical device of examples 1-11 or any combinations thereof, wherein the physiological electrical signal comprises an electrical signal of the heart.

Example 13

The implantable medical device of examples 1-12 or any combinations thereof, wherein the at least one electrode comprises tip electrode configured to contact cardiac tissue.

Example 14

A method for manufacturing an implantable medical device, the method comprising forming a first material of an electrode of the implantable medical device; depositing a mask on at least part of the first material; depositing a second material on the mask and the first material to form a higher-capacitance portion of the electrode; and removing the mask from the first material to expose a lower-capacitance portion of the electrode.

Example 15

The method of example 14, wherein the electrode comprises a first electrode, the method further comprising forming the first material of a second electrode of the implantable medical device; depositing a second mask on the first material of the second electrode; depositing the second material on the first material of the second electrode to form a higher-capacitance portion of the second electrode; and removing the second mask from the first material of the second electrode to expose a lower-capacitance portion of the second electrode.

Example 16

The method of examples 14-15 or any combinations thereof, further comprising forming an elongate housing of the implantable medical device, wherein the elongate housing includes a first end and second end opposite the first end; the first electrode is positioned on the elongate housing proximate the first end; the second electrode is positioned on the elongate housing proximate the second end; the higher-capacitance portion of the first electrode is closer to the first end than the lower-capacitance portion of the first electrode; and the second higher-capacitance portion is closer to the second end than the second lower-capacitance portion.

Example 17

The method of examples 14-16 or any combinations thereof, further comprising forming an elongate housing of the implantable medical device; and placing an antenna on or within the elongate housing, wherein the antenna is disposed between the first electrode and the second electrode; the lower-capacitance portion of the first electrode is positioned closer to the antenna than the higher-capacitance portion of the first electrode; and the second lower-capacitance portion is positioned closer to the antenna than the second higher-capacitance portion.

Example 18

The method of examples 14-17 or any combinations thereof, wherein the lower-capacitance portion comprises titanium or titanium dioxide; and the higher-capacitance portion comprises titanium nitride.

Example 19

The method of examples 14-18 or any combinations thereof, wherein the lower-capacitance portion is a larger percentage of a surface area of the at least one electrode than the higher-capacitance portion.

Example 20

The method of examples 14-19 or any combinations thereof, wherein the lower-capacitance portion is configured to transmit or receive TCC signals; and the higher-capacitance portion is configured to sense the physiological electrical signal and transmit or receive TCC signals.

Example 21

The method of examples 14-20 or any combinations thereof, wherein the lower-capacitance portion includes a capacitance of less than approximately forty nanofarads and greater than approximately three nanofarads; and the higher-capacitance portion includes a capacitance of greater than approximately two hundred nanofarads.

Example 22

A method for manufacturing an implantable medical device, the method comprising forming an electrode on the implantable medical device; depositing a mask on a first portion of the electrode; depositing a dielectric material on the mask and a second portion of the electrode; and removing the mask from the first portion of the electrode and leaving the dielectric material on the second portion of the electrode, wherein the first portion of the electrode has a higher capacitance than the second portion of the electrode.

Example 23

An implantable medical device comprising at least four electrodes; sensing circuitry configured to sense a physiological electrical signal via a first electrode and a second electrode of the at least four electrodes; communication circuitry configured to transmit a transconductance communication signal via at least a third electrode and a fourth electrode of the at least four electrodes; and switching circuitry configured to connect the first electrode and the second electrode to the sensing circuitry, and connect the at least four electrodes to the communication circuitry; and processing circuitry configured to control the switching circuitry to connect the first electrode and the second electrode to the sensing circuitry to sense the physiological electrical signal, and control the switching circuitry to connect at least the third electrode and the fourth electrode to the communication circuitry to transmit or receive TCC signals.

Example 24

The implantable medical device of example 23, further comprising an elongate housing that contains the sensing circuitry and the communication circuitry, the elongate housing including a first end and second end opposite the first end, wherein the first electrode is positioned on the elongate housing proximate the first end; the second electrode is positioned on the elongate housing proximate the second end; the first electrode is closer to the first end than the third electrode; and the second electrode is closer to the second end than the fourth electrode.

Example 25

The implantable medical device of examples 23-24 or any combinations thereof, wherein a surface area of the first electrode is smaller than a surface area of the third electrode; and a surface area of the second electrode is smaller than a surface area of the fourth electrode.

Example 26

A method for operating an implantable medical device, the method comprising controlling switching circuitry of the implantable medical device to connect a first electrode and a second electrode to sensing circuitry of the implantable medical device; sensing a physiological electrical signal via the first electrode and the second electrode; controlling the switching circuitry to connect at least a third electrode and a fourth electrode to communication circuitry of the implantable medical device; transmitting TCC signals via at least the third electrode and the fourth electrode; and receiving TCC signals via the at least two electrodes of the first electrode, the second electrode, the third electrode, and the fourth electrode.

Example 27

The method of example 26, wherein the first electrode is positioned on an elongate housing of the implantable medical device proximate a first end of the elongate housing; the second electrode is positioned on the elongate housing proximate a second end of the elongate housing; the first electrode is closer to the first end than the third electrode; and the second electrode is closer to the second end than the fourth electrode.

Example 28

The method of examples 26-27 or any combinations thereof, wherein a surface area of the first electrode is smaller than a surface area of the third electrode, and wherein a surface area of the second electrode is smaller than a surface area of the fourth electrode.

Example 29

The method of examples 26-28 or any combinations thereof, further comprising controlling the switching circuitry to connect the first electrode and the second electrode to signal generation circuitry of the implantable medical device; and delivering a therapy pulse via the first electrode and the second electrode.

Various aspects of this disclosure have been described. These and other aspects are within the scope of the following claims.

What is claimed is:
1. An implantable medical device comprising:
a plurality of electrodes;
sensing circuitry configured to sense a physiological electrical signal via the plurality of electrodes; and
communication circuitry configured to transmit and/or receive a transconductance communication signal via the plurality of electrodes,
wherein at least one electrode of the plurality of electrodes comprises a lower-capacitance portion and a higher-capacitance portion.
2. The implantable medical device of claim 1, wherein the plurality of electrodes comprises:
a first electrode including a first lower-capacitance portion and a first higher-capacitance portion; and
a second electrode including a second lower-capacitance portion and a second higher-capacitance portion.

3. The implantable medical device of claim 2, further comprising an elongate housing that contains the sensing circuitry and the communication circuitry, the elongate housing including a first end and second end opposite the first end, wherein:
the first electrode is positioned on the elongate housing proximate the first end;
the second electrode is positioned on the elongate housing proximate the second end;
the first higher-capacitance portion is closer to the first end than the first lower-capacitance portion; and
the second higher-capacitance portion is closer to the second end than the second lower-capacitance portion.

4. The implantable medical device of claim 2, further comprising an elongate housing and an antenna on or within the elongate housing, wherein:
the antenna is disposed between the first electrode and the second electrode;
the first lower-capacitance portion is positioned closer to the antenna than the first higher-capacitance portion; and
the second lower-capacitance portion is positioned closer to the antenna than the second higher-capacitance portion.

5. The implantable medical device of claim 2, wherein a distance between a center of the first electrode and a center of the second electrode is less than a distance between a center of the first higher-capacitance portion and a center of the second higher-capacitance portion.

6. The implantable medical device of claim 1, wherein:
the lower-capacitance portion includes titanium or titanium dioxide; and
the higher-capacitance portion includes titanium nitride.

7. The implantable medical device of claim 1, wherein:
the lower-capacitance portion is configured to transmit or receive tissue conductance communication (TCC) signals; and
the higher-capacitance portion is configured to sense the physiological electrical signal and transmit or receive TCC signals.

8. The implantable medical device of claim 7, further comprising signal generation circuitry configured to deliver a therapy pulse via the at least one electrode, wherein the higher-capacitance portion is configured to deliver the therapy pulse and the lower-capacitance portion is configured to not deliver the therapy pulse.

9. The implantable medical device of claim 1, wherein the lower-capacitance portion is a larger percentage of a surface area of the at least one electrode than the higher-capacitance portion.

10. The implantable medical device of claim 1, wherein:
the lower-capacitance portion includes a capacitance of less than approximately forty nanofarads and greater than approximately three nanofarads; and
the higher-capacitance portion includes a capacitance of greater than approximately two hundred nanofarads.

11. The implantable medical device of claim 1, further comprising a dielectric material at least partially covering at least one of the lower-capacitance portion or the higher capacitance portion.

12. The implantable medical device of claim 1, wherein the physiological electrical signal comprises an electrical signal of the heart.

13. The implantable medical device of claim 1, wherein the at least one electrode comprises a tip electrode configured to contact cardiac tissue.

14. An implantable medical device comprising:
at least four electrodes;
sensing circuitry configured to sense a physiological electrical signal via a first electrode and a second electrode of the at least four electrodes;
communication circuitry configured to transmit a transconductance communication signal via at least a third electrode and a fourth electrode of the at least four electrodes;
an elongate housing that contains the sensing circuitry and the communication circuitry, the elongate housing including a first end and second end opposite the first end, wherein:
the first electrode is positioned on the elongate housing proximate the first end;
the second electrode is positioned on the elongate housing proximate the second end;
the first electrode is closer to the first end than the third electrode; and
the second electrode is closer to the second end than the fourth electrode; and
switching circuitry configured to:
connect the first electrode and the second electrode to the sensing circuitry, and
connect the at least four electrodes to the communication circuitry; and
processing circuitry configured to:
control the switching circuitry to connect the first electrode and the second electrode to the sensing circuitry to sense the physiological electrical signal, and
control the switching circuitry to connect at least the third electrode and the fourth electrode to the communication circuitry to transmit or receive tissue conductance communication (TCC) signals.

15. The implantable medical device of claim 14, wherein:
a surface area of the first electrode is smaller than a surface area of the third electrode; and
a surface area of the second electrode is smaller than a surface area of the fourth electrode.

16. A method for operating an implantable medical device, the method comprising:
controlling switching circuitry of the implantable medical device to connect a first electrode and a second electrode to sensing circuitry of the implantable medical device;
sensing a physiological electrical signal via the first electrode and the second electrode;
controlling the switching circuitry to connect at least a third electrode and a fourth electrode to communication circuitry of the implantable medical device;
transmitting tissue conductance communication (TCC) signals via at least the third electrode and the fourth electrode; and
receiving TCC signals via the at least two electrodes of the first electrode, the second electrode, the third electrode, and the fourth electrode.

17. The method of claim 16, wherein:
the first electrode is positioned on an elongate housing of the implantable medical device proximate a first end of the elongate housing;
the second electrode is positioned on the elongate housing proximate a second end of the elongate housing;
the first electrode is closer to the first end than the third electrode; and
the second electrode is closer to the second end than the fourth electrode.

18. The method of claim 16, wherein a surface area of the first electrode is smaller than a surface area of the third electrode, and wherein a surface area of the second electrode is smaller than a surface area of the fourth electrode.

19. The method of claim 16, further comprising:
controlling the switching circuitry to connect the first electrode and the second electrode to signal generation circuitry of the implantable medical device; and
delivering a therapy pulse via the first electrode and the second electrode.

20. An implantable medical device comprising:
at least four electrodes;
sensing circuitry configured to sense a physiological electrical signal via a first electrode and a second electrode of the at least four electrodes;
communication circuitry configured to transmit a transconductance communication signal via at least a third electrode and a fourth electrode of the at least four electrodes, wherein a surface area of the first electrode is smaller than a surface area of the third electrode, and wherein a surface area of the second electrode is smaller than a surface area of the fourth electrode; and
switching circuitry configured to:
connect the first electrode and the second electrode to the sensing circuitry, and
connect the at least four electrodes to the communication circuitry; and
processing circuitry configured to:
control the switching circuitry to connect the first electrode and the second electrode to the sensing circuitry to sense the physiological electrical signal, and
control the switching circuitry to connect at least the third electrode and the fourth electrode to the communication circuitry to transmit or receive tissue conductance communication (TCC) signals.

21. An implantable medical device comprising:
a plurality of electrodes, wherein at least one electrode of the plurality of electrodes comprises a lower-capacitance portion and a higher-capacitance portion, and wherein the lower-capacitance portion is a larger percentage of a surface area of the at least one electrode than the higher-capacitance portion;
a dielectric material at least partially covering at least one of the lower-capacitance portion or the higher capacitance portion;
sensing circuitry configured to sense a physiological electrical signal via the plurality of electrodes; and
communication circuitry configured to transmit and/or receive a transconductance communication signal via the plurality of electrodes.

22. The implantable medical device of claim 21, wherein the plurality of electrodes comprises:
a first electrode including a first lower-capacitance portion and a first higher-capacitance portion; and
a second electrode including a second lower-capacitance portion and a second higher-capacitance portion.

23. The implantable medical device of claim 22, further comprising an elongate housing that contains the sensing circuitry and the communication circuitry, the elongate housing including a first end and second end opposite the first end, wherein:
the first electrode is positioned on the elongate housing proximate the first end;
the second electrode is positioned on the elongate housing proximate the second end;
the first higher-capacitance portion is closer to the first end than the first lower-capacitance portion; and
the second higher-capacitance portion is closer to the second end than the second lower-capacitance portion.

24. The implantable medical device of claim 22, further comprising an elongate housing and an antenna on or within the elongate housing, wherein:
the antenna is disposed between the first electrode and the second electrode;
the first lower-capacitance portion is positioned closer to the antenna than the first higher-capacitance portion; and
the second lower-capacitance portion is positioned closer to the antenna than the second higher-capacitance portion.

25. The implantable medical device of claim 22, wherein a distance between a center of the first electrode and a center of the second electrode is less than a distance between a center of the first higher-capacitance portion and a center of the second higher-capacitance portion.

26. The implantable medical device of claim 21,
wherein the lower-capacitance portion includes titanium or titanium dioxide, and
wherein the higher-capacitance portion includes titanium nitride.

27. The implantable medical device of claim 21,
wherein the lower-capacitance portion is configured to transmit or receive tissue conductance communication (TCC) signals, and
wherein the higher-capacitance portion is configured to sense the physiological electrical signal and transmit or receive TCC signals.

28. The implantable medical device of claim 21,
the lower-capacitance portion includes a capacitance of less than approximately forty nanofarads and greater than approximately three nanofarads; and
the higher-capacitance portion includes a capacitance of greater than approximately two hundred nanofarads.

* * * * *